(12) United States Patent
Rhyu et al.

(10) Patent No.: US 9,301,989 B2
(45) Date of Patent: Apr. 5, 2016

(54) HTRPA1-ACTIVATING COMPOSITION AND USE THEREOF

(71) Applicant: KOREA FOOD RESEARCH INSTITUTE, Gyeonggi-do (KR)

(72) Inventors: Mee Ra Rhyu, Gyeonggi-do (KR); Hee Jin Son, Gyeonggi-do (KR); Yi Seul Kim, Gyeonggi-do (KR); Min Jung Kim, Seoul (KR); Hye Young Kim, Seoul (KR); Jae-Ho Park, Gyeonggi-do (KR)

(73) Assignee: KOREA FOOD RESEARCH INSTITUTE, Gyeonggi-Do (KR)

( * ) Notice: Subject to any disclaimer, the term of this patent is extended or adjusted under 35 U.S.C. 154(b) by 0 days.

(21) Appl. No.: 14/365,582

(22) PCT Filed: Nov. 9, 2012

(86) PCT No.: PCT/KR2012/009483
§ 371 (c)(1),
(2) Date: Jun. 13, 2014

(87) PCT Pub. No.: WO2013/073801
PCT Pub. Date: May 23, 2013

(65) Prior Publication Data
US 2014/0322366 A1 Oct. 30, 2014

(30) Foreign Application Priority Data

| Nov. 18, 2011 | (KR) | 10-2011-0121155 |
| Jun. 27, 2012 | (KR) | 10-2012-0068889 |
| Jun. 27, 2012 | (KR) | 10-2012-0068890 |
| Jun. 27, 2012 | (KR) | 10-2012-0068891 |

(51) Int. Cl.

| A01N 65/00 | (2009.01) |
| A61K 36/8962 | (2006.01) |
| A61K 36/31 | (2006.01) |
| A61K 36/896 | (2006.01) |
| A61K 36/21 | (2006.01) |
| A61K 36/23 | (2006.01) |
| A61K 36/28 | (2006.01) |
| A61K 36/53 | (2006.01) |
| A61K 31/085 | (2006.01) |
| A61K 36/236 | (2006.01) |
| A61K 36/25 | (2006.01) |
| A61K 36/288 | (2006.01) |
| A61K 36/532 | (2006.01) |
| A61K 36/533 | (2006.01) |
| G01N 33/50 | (2006.01) |

(52) U.S. Cl.
CPC .......... *A61K 36/8962* (2013.01); *A61K 31/085* (2013.01); *A61K 36/21* (2013.01); *A61K 36/23* (2013.01); *A61K 36/236* (2013.01); *A61K 36/25* (2013.01); *A61K 36/28* (2013.01); *A61K 36/288* (2013.01); *A61K 36/31* (2013.01); *A61K 36/53* (2013.01); *A61K 36/532* (2013.01); *A61K 36/533* (2013.01); *A61K 36/896* (2013.01); *G01N 33/5097* (2013.01); *G01N 2500/04* (2013.01)

(58) Field of Classification Search
CPC ...................................................... A61K 36/00
USPC .......................................................... 424/725
See application file for complete search history.

(56) References Cited

U.S. PATENT DOCUMENTS

2008/0050750 A1 2/2008 Lee et al.

FOREIGN PATENT DOCUMENTS

KR 10-2001-0031501 A 4/2001

OTHER PUBLICATIONS

International Search Report for PCT/KR2012/000483.
MacPherson LJ. et al. "The Pungency of Garlic: Activation of TRPA1 and TRPV1 in Response to Allicin", Current Biology, vol. 15, May 24, 2005, pp. 920-934 (See p. 933, conclusion.).
Rhyu Meera et al., European Chemoreception Research Organization Congress 2011, pp. 1-170 (See p. 80.).

*Primary Examiner* — Michael Meller

(57) ABSTRACT

A coniferyl alcohol or a Compositae family, Brassicaceae family, Umbelliferae family, Lamiaceae family, Liliaceae family or Amaranthaceae plant extract provides various uses associated with hTRPA1 activation, and, being a natural compound, involves relatively few side effects in the body and has substantial industrial applicability. The coniferyl alcohol or the Compositae family, Brassicaceae family, Umbelliferae family, Lamiaceae family, Liliaceae family or Amaranthaceae plant extract of the present invention not only will be a novel medical or food raw material which is helpful in maintaining homeostasis in the body associated with hTRPA1 activation, but can also be used to advantage in hTRPA1 antagonist screening.

2 Claims, 37 Drawing Sheets

A

B

Structures of hederagenin saponins    Structures of phenolic compounds

HTRPA1-ACTIVATING COMPOSITION AND USE THEREOF

CROSS REFERENCE TO RELATED APPLICATIONS AND CLAIM OF PRIORITY

This patent application is a National Phase application under 35 U.S.C. §371 of International Application No. PCT/KR2012/009483, filed 9 Nov. 2012, which claims priority to Korean Patent Application Nos. 10-2011-0121155 filed 18 Nov. 2011, 10-2012-0068889 filed 27 Jun. 2012, 10-2012-0068890 filed 27 Jun. 2012, and 10-2012-0068891 filed 27 Jun. 2012, entire contents of which are incorporated herein by reference.

TECHNICAL FIELD

The present invention relates to a composition for activating transient receptor potential cation channel, subfamily A, member 1 (TRPA1) and a use thereof.

BACKGROUND ART

Transient receptor potential cation channel, subfamily A, member 1 (TRPA1) is a nonselective cation channel that belongs to a superfamily of the TRP ion channel. Like other family members, the TRPA1 channel is formed by tetramerization of 4 subunits each including six transmembrane domains, a pore loop, and intracellular N- and C-termini. TRPA1 is expressed in sensory neurons, and co-localized with pain markers such as TRPV1, calcitonin gene-related peptide and bradykinin receptor (Nagata, K. et al., Journal of Neuroscience 2005, 25, 4052-4061; Story, G. M. et al., Cell 2003, 112, 819-829; Corey, D. P. et al., Nature 2004, 432, 723-730; Bautista, D. M. et al., Proceedings of the National Academy of Science U.S.A. 2005, 102, 12248-12252; Jaquemar, D. et al., Journal of Biological Chemistry 1999, 274, 7325-7333).

In pain models, the knockdown of TRPA1 inhibited cold hyperalgesia induced by inflammation and nerve injury (Obata, K. et al., Journal of Clinical Investigation 2005, 115, 2393-2401; Jordt, S. E. et al., Nature 2004, 427, 260-265; Katsura, H. et al., Exploratory Neurology 2006, 200, 112-123). In addition, the TRPA1 gene knockdown caused impaired sensory functions and deficits in bradykinin-evoked pain hypersensitivity (Kwan, K. Y. et al. Neuron 2006, 50, 277-289; Bautista, D. M. et al. Cell 2006, 124, 1269-1282).

The above experimental results suggest that TRPA1 plays important roles in sensory functions and pain states.

Meanwhile, the recent experimental results have showed that TRPA1 agonists directly interact with TRPA1. It has been reported that AITC and cinnamaldehyde covalently modify cysteine and lysine residues in the N terminus of TRPA1 and activate this channel (Hinman, A., Chuang, H. H., Bautista, D. M., and Julius, D. Proceedings of the National Academy of Science U.S.A. 2006, 103, 19564-19568; Macpherson, L. J., Dubin, A. E., Evans, M. J., Marr, F., Schultz, P. G., Cravatt, B. F., and Patapoutian, A., Nature 2007, 445, 541-545).

Meanwhile, among Korean aromatic plants which cause pungent chemosensation, such as spicy, tingle, and tangy tastes, sprouts of *Kalopanax pictus* (English name: Carstor Araila) (*Kalopanax pictus* sprout, hereinafter, referred to as KPs) corresponds to a naturally growing plant that has been widely used in food, such as wild greens and spices. *Kalopanax pictus* is a plant that belongs to the Acanthopanax family, and the bark of *Kalopanax pictus* is referred to as *Kalopanax*, which has been used for neuralgia, arthritis, and diabetes. The main constituent of *Kalopanax* is saponin, and its phenol-based materials have been found to be syringin, coniferyl aldehyde glucoside, liriodendrin, and the like. It has been known that the similar constituents are also present in the leaves. Saponin is mainly hederagenin glycoside, and has a kalopanaxsaponin-based material composed of monodesmoside and bisdesmoside. Meanwhile, in Korea, sprouts of *Kalopanax pictus* is commonly called *Kalopanax pictus* shoots, which is used for wild greens. The leaves of *Kalopanax pictus* are not edible since the leaves become rough and has changed flavor as the season goes on, but sprouts have been widely used for foods.

The Compositae plants, which are the most evolved plant taxonomic group in dicotyledoneae, have 23,000 species which are the most widely distributed over the world. Among them, 17 species grow naturally in Korea. Medicinal plants of the family Compositae, such as wormwood, wild aster, *Chrysanthemum zawadskii*, safflower, and atractylodes, have been considered to be sacred herbs for external youth, and have been widely used as food, medicine, brewing, and for ornamental purposes since ancient times. With respect to taxonomic characteristics of the family Compositae, leaves grow in opposite, alternate, or in rare cases, verticillate form, and may have a single-leaf or compound-leaf type, but do not have stipules.

Studies on the functionality of wormwood, which is the member of the Compositae family, have been the most reported. Wormwood is not only used as an antihemorrhagic in Oriental medicine, but has also been reported to have efficacy in digestion, deworming, odor removal, gastroenteropathy, constipation, neuralgia, gynecological disorders, and the like. Also, studies on the search for and analysis of functional materials of *Youngia sonchifolia, Lactuca raddeana, Xanthium strumarium*, and *Cirsium japonicum* have been conducted. The search for and product development with respect to functional bioactivity of the Compositae plants have mainly been restricted to flowers. However, the different parts of the plant have different functional bioactivities, and the whole plant is equally used when being used as raw vegetables or wild greens for food, and thus these facts need to be considered.

As such, the Compositae plants have excellent pharmacological effects, and thus have been used as edible and medicinal plants in the East and West and have been actively studied in association with their functional bioactivities including antioxidant activity, immunity enhancing activity, and the like. However, there are few studies about "taste", which is the most important factor of determining its value as food.

The Labiatae family plants grow mainly in the Mediterranean and the West Asia, and have been known to include 200 genera and about 3,200 species distributed all over the world. In Korea, 25 genera and 3,200 species of herbs, such as *Mosla punctulata*, mint, *Stachys riederi*, perfumed oil, *Agastache rugosa*, and *Leonurus sibiricus* are distributed, and the whole plant is covered with pili that emit special favors. The Labiatae plants contain beautiful flowers and flavors, and thus many species are cultivated for ornamental purposes, and are also used as the raw materials of favorite foods and spices. Essential oils abundant in the family Labiatae have pharmacological effects such as immunity enhancement, anti-cancer activity, and anti-aging activity, and antiviral and antioxidant activities, and thus, studies about the use of the essential oils have been actively conducted in the industries of medicine, food, and cosmetics.

Among these Labiatae family plants, motherwort refers to the whole plant of annual or biennial motherwort growing in a house or in the wild. The meaning of motherwort is wort that is beneficial to women, and the western motherwort *L. cardiac* (mother wort) is also said to have the same meaning as the Oriental motherwort. Motherwort improves the flow of blood and removes the stasis of blood, and thus is well known as an effective medicine in the gynecology for treating disease symptoms, such as irregular menstruation, menoschesis, postpartum abdominal pain, dysuria, edema, Changongjongdok, itch, polydipsia, and postpartum hemorrhage. The main ingredient of the motherwort is alkaloid leonurine, and it also contains stachydrine, leonurine, lutine as flavonoids, and the like. The motherwort has been reported to contain, as other organic acids, benzoic acid, lauric acid, essential fatty acid linoleic acid, and oleic acid, and also contains arginine, 4-guanidino-1-butanoic acid, stachyose, vitamin A, and the like.

The *Agastache rugosa* used herein, which is a perennial herb of the family Labiatae, forms a colony after attachment, and is able to grow even on barren fields and mountains. Geographically, the *Agastache rugosa* grows in Northeast Asia, and it is an indigenous food resource that grows in the wild or is also cultivated in the southern area of Korea. Traditionally, the leaves of *Agastache rugosa*, called bandanna, have been used for a long time as spices for loach soup, various stews, or pancakes, and the flowers of *Agastache rugosa* have also been utilized as a source of nectar. In addition, in Oriental medicine, the above-ground part of *Agastache rugosa* is called Gwakhyang, and has been used as an important medicinal ingredient in water intoxication, Geoakgi, Jigwaklan, Yopung, Chibiwitoyeog, and the like. In addition, the underground part of *Agastache rugosa* is called Gwakhyangeun, and has been used for the treatment of vomiting, dysentery, pricking pain, cholera morbus, and the like. An essential oil ingredient obtained by distilling Gwakhyang is called Gwakhyangro, and has been used for the treatment of heart Burn, nausea, stagnation, and the like, due to summer heat. As described above, the *Agastache rugosa* is an agricultural resource that will be widely utilized in the future since the whole plant has been already used for food or medicine. As described above, the leaves, flowers, roots, stems, and fruits of these Labiatae plants have unique flavors and tastes, and thus function as an herb (aromatic plant) that is used mainly as spices, antioxidant agents, and the like, and have been used as food and medicine, and for ornamental purposes.

*Allium ochotense* Prokh., which is a perennial plant of the genus *Allium* of the Liliaceae family, is distributed in the mountains of Asia and America and in the Himalayas, and naturally grows mainly in the Ulleungdo Island, Jiri Mountain, Odae Mountain, Seorak Mountain, and the like in Korea. *Allium ochotense* Prokh. has a strong garlic smell and very similar pharmacognostical uses to garlic. Although *Allium ochotense* Prokh. belongs to the genus *Allium* like garlic, its shape is completely different from that of garlic. In Korea, bulbs sprout in fallen leaves in March and April after the winter, and young leaves and stems are taken and used for food in May. They are highly palatable due to their unique garlic favor and taste and excellent nutritional characteristics. The leaves and stems are produced once per year in a natural state, and the whole plant including bulbs, flowers, and the like as well as the leaves is used. According to results of studies on ingredients of *Allium ochotense* Prokh., the leaves contain 2-3% of hydrocarbon and ascorbic acid, and the bulbs have been reported to contain an S-alkenyl- or S-alkyl-L-cystein type compound in sulfur-containing compounds that have a platelet aggregation inhibitory effect. In addition, it has been reported that spirotanol glycoside type gitogenin 3-O-lycotetroside, flavonoid glycoside type astragalin and kaempferol 3,4″-di-O-β-D-glucoside, flavonol type kercetin and kaempferol, and ferulic acid as a phenylpropanoide-based compound was isolated from an extract of the whole plant. In the past, *Allium ochotense* Prokh. was used as an emergency crop on Ulleungdo Island and thus called myeonguinamul or myeonginamul, and has been well known as a traditional stamina food, like garlic. In addition, *Allium ochotense* Prokh. has been used for hypertension, arteriosclerosis, gastritis, constipation, abdominal pain, forgetfulness, insomnia, and the like, and the demand therefor has recently increased considerably with the spread of the social well-being mood. However, *Allium ochotense* Prokh. has not been well researched as compared with garlic, onions, and leeks, which are representative plants of the genus *Allium* to which *Allium* ochotense Prokh. belongs, and the existing research on *Allium* ochotense Prokh. is mainly about vegetation distribution and cultivation of *Allium ochotense* Prokh. produced on Ulleungdo Island which is the main production area.

*Allium macrostemon* Bunge similar to *Allium ochotense* Prokh. is also a perennial bulbous plant that belongs to the genus *Allium* of the Liliaceae family, and widely distributed in Northeast Asia regions including Japan, China, Mongolia, as well as Korea, and grows naturally in hills around the country of Korea. *Allium macrostemon* Bunge has been widely used for a long time since its unique flavor and taste matches the Korean's preference, and is still used as an appetizing food in spring. According to records of the Heritage of the Three States, the use of *Allium macrostemon* Bunge as food is estimated to have been started in that period. It has been reported that *Allium macrostemon* Bunge has high utility as an emergency food and thus is called 'Vida'. In addition, *Allium macrostemon* Bunge has been used as a medicinal plant, and the bulbs of *Allium macrostemon* Bunge have been used for a strong stomach, colon health, and burn treatment. As for *Allium macrostemon* Bunge, the entire living body is edible, and the whole plant has been known to be abundant in inorganic ingredients, such as calcium, phosphorus, and iron, amino acids, sugars, and vitamins. *Allium macrostemon* Bunge has very high values in food and nutritional aspects since its leaf contains large amounts of inorganic ingredients and its bulb and root contain many kinds of amino acids and sugars. As described above, the demands of *Allium ochotense* Prokh. and *Allium macrostemon* Bunge are increasing as the food consumption structure is gentrified and verified due to the improvement of dietary standards. However, *Allium ochotense* Prokh. and *Allium macrostemon* Bunge have not been well researched out of plant encyclopedias and taxonomic studies, and research on *Allium ochotense* Prokh. and *Allium macrostemon* Bunge has been recently limited to plant culturing, ingredient analysis, and functional characteristics.

The Amaranthaceae family, which belongs to the Order Caryophyllaes, includes about 160 genera and 2,400 species. According to the APG II classification system, the species traditionally classified in the family Chenopodiaceae are also classified in the family Amaranthaceae. As for *Amaranthus mangostanus*, which is an annual plant of the family Amaranthaceae native to India, the stem has no hair, is straightly erected, and is about 1 m in length, and the leaves are alternately arranged in an egg-shaped diamond manner and have long leafstems. From summer through fall, small white-green flowers bloom on ends of branches or axils in an Isaac inflorescence manner, and these blooms put together, and the fruit belongs to dehiscent fruit and has an oval shape. *Amaranthus mangostanus* is also planted for ornamental purposes, and its young leaves are edible.

The Labiatae, Liliaceae, and Amaranthaceae family plants have excellent pharmacological effects, and thus have been used as edible and medicinal plants in the East and the West, and have been actively studied in association with their functional bioactivities including antioxidant activity, immunity enhancing activity, and the like. However, the studies about "taste" are not non-existent.

The Brassicaceae family plants include 350 genera and 3,000 species, and are mainly distributed in the temperature zone and the warm temperature zones of the Northern Hemisphere, and particularly, there are many kinds of Brassicaceae plants in the West Asia to the Mediterranean coastal areas. The Brassicaceae family vegetables, which are heavily cultivated in Korea, are known to be cabbage, Chinese cabbage, kale, cauliflower, broccoli, turnip, radish, rapeseed, horseradish, and the like. The distinctively pungent tastes and flavors of these vegetable are mainly due to the sulfur-containing compound isothiocyanates, and have relevance to some sulfides. The Brassicaceae family vegetables and some chemical compounds contained in the Brassicaceae family have been known to exhibit chemoprotection effects against carcinogenesis, and particularly, to induce activities of stage I and stage II enzymes acting as detoxifying enzymes.

The *Wasabia* Matsum. is one of the smallest genus groups in the family Brassicaceae, and 20,000 species are distributed in only the East Asia over the world. The genus *Wasabia* Matsum. is differentiated from plants of the other genera due to its characteristics since flowers are white, pieces of the silique are not entangled while dehiscing, the flowers have bracts, seeds are large, the number of seeds is small, and seed leaves are not leaned. Korea has one species of *Wasabia* Matsum. Wasabi is recognized as the same species as that distributed in Japan and thus *Wasabia japonica* (Miq.) Matsum. is used for the binomial name thereof, and is also called wasabi. *Wasabia japonica* (Miq.) Matsum. is highly used as a seasoning sauce for fish and meat dishes due to its distinctive spicy taste. *Wasabia japonica* (Miq.) Matsum. has been recently used as a seasoning, for various foods and beverages including Kimchi, pickled foods, fried foods, fried foods, drinks, and ice cream, and also air fresheners, food preservatives, and the like, in Japan which is one of the main consumption nations of *Wasabia* Matsum. The reason is that *Wasabia japonica* (Miq.) Matsum. has been increasingly used since the isocyanate contained in *Wasabia* Matsum. is researched and reported to have sterilizing, insecticidal, platelet aggregation inhibiting, anti-cancer, anti-aging, and antioxidant functions as well as an appetite promoting function. Recently, there are increasing cases in which leaves of *Wasabia japonica* (Miq.) Matsum. are used as wrapping vegetables or eaten in pickled form.

Mustard greens or leaf mustard, having similar characteristics as Wasabi, are leaves of *Brassica juncea*, brown mustard, or indian mustard, and are one kind of leaf vegetables. Leaf mustard is salted and fermented to be edible as Kimchi, and seeds thereof have been used as a spice. Leaf mustard is originally from China, and, at present, widely cultured in Korea, Japan, and the like. Leaf mustard has been cultivated for a long time in the Dolsan district of Yeocheon-gun, Jeollanam-do, Korea, and has a distinctive taste predominated by the unique local climates, soil conditions, and the like, so that a lot of leaf mustard is supplied to large cities or other provinces for Kimchi making. The distinctively pungent tastes of the leaf mustard is also mainly due to a volatile sulfur-containing ingredient, isocyanate, which has been reported to be produced by action of thioglucoside glucohydrolase on glucocynolates such as sinigrin.

The Umbelliferae (or Apiaceae) family plants include about 2500-3000 species that naturally grow over the world, and have been reported to include 68 species growing in Korea. The family Umbelliferae plants are differently described in each book, and in some cases, the terms associated therewith do not match and the systemic research thereon is insufficient. In addition, it has been well known that the family Umbelliferae plants are difficult to classify due to their similar features. Most of the family Umbelliferae plants have distinctive flavors, and thus, in many cases, are eaten as a spice, wild greens, or the like. Of these, water parsley (*Oenanthe javanica* (Blume) DC.) is a perennial herb that belongs to the family Umbelliferae, grows naturally in wetlands, distributed in Korea, Japan, China, Taiwan, Malaysia, India, and the like, and cultured in the farms. Water parsley is a representative alkali food that contains vitamins, potassium, calcium, and iron, as well as flavonoid compounds, in terms of food and nutritional point. Water parsley, which is much eaten, has been used in Kimchi, cooked greens, and small rolls of boiled parsley. In addition, water parsley is a plant that has high usability as a material for functional foods or spices due to its distinctive flavor and pharmacological actions. Similar to this, *Pleurospermum camtschaticum* Hoffm. is one of the plants eaten as pickled vegetables or wild greens due to its distinctive flavor. *Pleurospermum camtschaticum* Hoffm. is a perennial herb that belongs to the family Umbelliferae. As for external characteristics of *Pleurospermum camtschaticum* Hoffm., the height is about 50-100 cm, white flowers bloom in June and July, one stem has three leaves, and egg-shaped fruits are produced after the flowers fall. In folk remedies, *Pleurospermum camtschaticum* Hoffm. has been known to improve digestion, thereby stimulating appetite and helping make better maternal milk, and also have a cholesterol lowering function. *Pleurospermum camtschaticum* Hoffm. has been eaten by collecting soft leaf stems from mid-April to early May and then dipping them in sauce or seasoning them with condiments. *Pleurospermum camtschaticum* Hoffm. has been reported to have more carbohydrates, ash, phosphorus, and particularly, vitamin A as compared with celery which has a similar taste. *Ligusticum tachiroei* (Franch. & Sav.) M.Hiroe & Constance growing in gaps between wet rocks deep in the mountains has its distinctive flavor characteristics, is mainly used as a medicinal plant that treats erectile dysfunction, epilepsy, toothaches, and gynecopathy, rather than as raw vegetables or wild greens, and is distributed in Jeju Island, Jeollanam-do, Gyeongsangnam-do, Pyeonganbuk-do, Hamgyeongnam-do, and Hamgyeongbuk-do provinces.

As described above, research about wild vegetables of the families Brassicaceae and Umbelliferae, which have been widely used due to their distinctive flavor characteristics, are mainly restricted to their taxonomic characteristics or active ingredients. However, there is little research about their "taste", which is one of the most important factors for determining values thereof as food.

Research about "taste", which is one of the most important factors for determining a food value includes a wide variety of academic fields covering areas from molecular-level basic research to consumer and industrial applications. When a taste material is received in a receptor present in taste cells in taste buds, the generated signal is transmitted to central nerves through a taste nerve transmission passage. The central nerves process information of the signal and then perceive the signal. In other words, the taste material is recognized through a series of kinetic mechanisms from the peripheral nerves to the central nerves. Recently, substantial molecules of the taste receptor have been found with the development of molecular biology and related fields, and some G protein-coupled receptors (GPCR) and transient receptor potential (TRP) cation channel receptors have been cloned. Recently, cell-level research using the cloned receptors has become possible Through the researching technique using the cloned receptors, in vitro screening or sensory analysis techniques of new taste-activating substances have experienced breakthrough evolutions, and the most advanced, new methods, which have been used for the development of new drugs, can be applied to researches about food taste. Currently, food research about taste ingredients in a receptor level is nearly non-existent in Korea and is only in the beginning phase globally.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a novel material helpful to maintain homeostasis in the body in association with hTRPA1 activation. As a result, the present inventors have established that coniferyl alcohol contained in an extract and a fraction of *Kalopanax pictus* sprouts, or an extract of the Compositae, Labiatae, Liliaceae, Amaranthaceae, Brassicaceae, or Umbelliferae family plant is associated with hTRPA1 activation, and then have completed the present invention.

Accordingly, an aspect of the present invention is to provide a composition for activating hTRPA1.

Another aspect of the present invention is to provide a pungent flavor composition for activating hTRPA1.

Another aspect of the present invention is to provide anti-obesity composition for activating hTRPA1.

Another aspect of the present invention is to provide a method for screening an hTRPA1 antagonist.

Another aspect of the present invention is to provide a method for activating hTRPA1.

Another aspect of the present invention is to provide a lacrimatory composition for activating hTRPA1.

Other purposes and advantages of the present invention will be clarified by the following detailed description of the invention, claims, and drawings.

Technical Solution

In accordance with an aspect of the present invention, there is provided a composition for activating human transient receptor potential A1 (hTRPA1), the composition including coniferyl alcohol as an active ingredient or an extract of at least one selected from the group consisting of: (i) Compositae family plants consisting of *Ligularia fischeri* (Ledeb). Turcz., *Lactuca india* L., *Dendranthema zawadskii* var. *latilobum* (Maxim.) Kitam., and *Taraxacum platycarpum* Dahlst., (ii) Brassicaceae family plants consisting of *Wasabia japonica* (Miq.) Matsum. and *Brassica juncea* (L.) Czern. et coss, (iii) Umbelliferae family plants consisting of *Pleurospermum camtschaticum* Hoffm., *Ligusticum tachiroei* (Franch. & Sav.) M.Hiroe & Constance, and *Oenanthe javanica* (Blume) DC., (iv) Labiatae family plants consisting of *Leonurus japonicus* Houtt. and *Agastache rugosa* Kuntze, (v) Liliaceae family plants consisting of *Allium ochotense* Prokh. and *Allium macrostemon* Bunge, and (vi) *Amaranthus mangostanus* L.

In accordance with another aspect of the present invention, there is provided a method for activating human transient receptor potential A1 (hTRPA1), the method including: administering to a subject a therapeutically effective amount of a coniferyl alcohol as an active ingredient, or a therapeutically effective amount of an extract of at least one selected from the group consisting of: (i) Compositae family plants consisting of *Ligularia fischeri* (Ledeb). Turcz., *Lactuca india* L., *Dendranthema zawadskii* var. *latilobum* (Maxim.) Kitam., and *Taraxacum platycarpum* Dahlst., (ii) Brassicaceae family plants consisting of *Wasabia japonica* (Miq.) Matsum. and *Brassica juncea* (L.) Czern. et coss, (iii) Umbelliferae family plants consisting of *Pleurospermum camtschaticum* Hoffm., *Ligusticum tachiroei* (Franch. & Sav.) M.Hiroe & Constance, and *Oenanthe javanica* (Blume) DC., (iv) Labiatae family plants consisting of *Leonurus japonicus* Houtt. and *Agastache rugosa* Kuntze, (v) Liliaceae family plants consisting of *Allium ochotense* Prokh. and *Allium macrostemon* Bunge, and (vi) *Amaranthus mangostanus* L.

The present inventors have endeavored to develop a novel material helpful to maintain homeostasis in the body in association with hTRPA1 activation. As a result, the present inventors have established that coniferyl alcohol contained in an extract and a fraction of *Kalopanax pictus* sprouts, or an extract of the Compositae, Labiatae, Liliaceae, Amaranthaceae, Brassicaceae, or Umbelliferae family plant is associated with hTRPA1 activation.

According to a preferable embodiment of the present invention, the composition of the present invention induces a pungent flavor by activating hTRPA1.

Since the connection between hTRPA1 activation and a pungent flavor is described in many documents, the following example data suggesting that coniferyl alcohol or an extract of the Compositae, Labiatae, Liliaceae, Amaranthaceae, Brassicaceae, or Umbelliferae family plant strongly activates hTRPA1 sufficiently support a use of the plant extract as a pungent flavor agent. Allyl isothiocyanate (AITC), which is a mustard oil component as a pungent flavor agent (Bandell M, et al., Neuron 41:849-857 (2004)); Jordt S E et al., Nature 427:260-265 (2004)), has been well known as TRPA1 agonist. Also, cinnamaldehyde in cinnamon, allicin and diallyl sulfide derived from garlic and onion, carvacrol in oregano, isovelleral, and polygodial in water pepper and Tasmanian pepper are pungent flavor components, and have been known as TRPA1 agonists (Bandell M et al, Neuron 41:849-857 (2004); Bautista D M et al., Proc Natl Acad Sci USA 102: 12248-12252 (2005); Escalera J et al., J Biol Chem 283: 24136-24144 (2008); Macpherson L J et al., Curr Biol 15: 929-934 (2005); Xu H et al., Nat Neurosci 9: 628-635 (2006)).

The pungent flavor according to the composition of the present invention is refers to a 'taste' that is sensitized through a sense of taste, and the sense of taste is a way to feel a taste by an action of chemical receptors of the tongue, oral mucosa, and the larynx. The chemical receptors have taste buds as a sensory organ for feeling tastes. Very fine villi sprout from surfaces of the taste buds, and ions or molecules for tastes pass through ion channels in the cell membrane via small openings called taste pores. Sweet, bitter, salty, sour, and umami tastes, which are primary tastes, are recognized by the above-mentioned receptors, and pungent taste, astringent taste, and the like are sensations that are complexly felt through receptors, autonomic nerves in the mouth, or the mucous membrane of the tongue. For example, the pungent flavor (spicy, tingle, or tangy taste) is a sort of sensation of pain, which is felt by autonomic nerves in the mouth.

It has been reported that materials having pungent tastes expressed by spicy taste, refreshing taste, tingling taste, tangy taste, or the like, amongst the above-described tastes, activate TRP-based cation channels, e.g., hTRPA1. TRP-based receptors, which are typical cellular sensors to external stimuli, have important roles on other bioactive mechanisms, and thus, materials activating the TRP-based receptors are very important in this respect.

Preferably, the pungent flavor composition of the present invention is characterized by inducing spicy taste (pungency), tangy taste (acrid), or a combination thereof.

According to a preferable embodiment of the present invention, coniferyl alcohol or an extract of the Compositae, Labiatae, Liliaceae, Amaranthaceae, Brassicaceae, or Umbelliferae family plant has an effect of preventing, treating, or ameliorating obesity by activating hTRPA1.

Therefore, according to another aspect of the present invention, the present invention provides a composition containing coniferyl alcohol or an extract of the Compositae, Labiatae, Liliaceae, Amaranthaceae, Brassicaceae, or Umbelliferae family plant for preventing, treating, or ameliorating obesity.

Since the connection between hTRPA1 activation and obesity prevention is described in some documents, the following example data suggesting that coniferyl alcohol or an extract of the Compositae, Labiatae, Liliaceae, Amaranthaceae, Brassicaceae, or Umbelliferae family plant strongly activates hTRPA1 sufficiently support that a composition, an active ingredient, containing coniferyl alcohol or an extract of the Compositae, Labiatae, Liliaceae, Amaranthaceae, Brassicaceae, or Umbelliferae family plant induces the gastric stasis, to have a anti-obesity action through appetite suppression.

According to a preferable embodiment of the present invention, the coniferyl alcohol activates Htrpal and promotes the secretion of glucagon-like peptide-1 (GLP-1), thereby having an effect of preventing or treating diabetes, obesity, hypertension, atherosclerosis, or myocardial infarction.

Tatsuo Watanabe et al., *Recent Researches in Modern Medicine*, ISBN:978-960-474-278-3, p. 460-462 (2011) suggests that TRPA1 activation of TRPA1 agonists (e.g., pepper extract, piperine, or cinnamaldehyde) inhibits the accumulation of abdominal fat by enhancing in vivo energy metabolism. In addition, Doihara H et al., *Naunyn Schmiedebergs Arch Pharmacol.* 380(4):353-7 (2009) discloses that TRPA1 agonists induce the gastric stasis, resulting in appetite suppression.

Meanwhile, glucagon-like-peptide-1 (GLP-1) is a proglucogon-derived peptide secreted from intestinal L-cells in response to nutrient ingestion (Drucker, D J: The Glucagon-Like Peptides. Diabetes 47:159-169 (1998)). GLP-1 acts to stimulate the secretion of insulin from beta-cells of pancreas. In addition, GLP-1 acts to inhibit both gastric emptying and food intake. Due to these effects, GLP-1 and its agonist (e.g., GLP-1 secretagogue) are used to treat diabetes (particularly, type 2 diabetes, Toft-Nielsen M, et al., "Determinants of the effectiveness of glucagon-like peptide-1 in type 2 diabetes". *J Clin Endocrinol Metab* 86(8):3853-60 (2001)), obesity (Hayes M R et al., Comparative effects of the long-acting GLP-1 receptor ligands, liraglutide and exendin-4, on food intake and body weight suppression in rats. *Obesity* (Silver Spring). July; 19(7):1342-9 (2011), hypertension (Tanaka T et al., The role of incretins in salt-sensitive hypertension: the potential use of dipeptidyl peptidase-IV inhibitors. *Curr Opin Nephrol Hypertens*. September; 20(5):476-81 (2011)); atherosclerosis (Arakawa M et al., Inhibition of monocyte adhesion to endothelial cells and attenuation of atherosclerotic lesion by a glucagon-like peptide-1 receptor agonist, exendin-4; *Diabetes*. April; 59(4):1030-7 (2010); Rizzo M et al, Glucose lowering and anti-atherogenic effects of incretin-based therapies: GLP-1 analogues and DPP-4-inhibitors. *Expert Opin Investig Drugs*. October; 18(10):1495-503 (2009)); and myocardial infarction (Ku H C et al., DPP4 deficiency preserves cardiac function via GLP-1 signaling in rats subjected to myocardial ischemia/reperfusion. Naunyn Schmiedebergs Arch Pharmacol. August; 384(2):197-207 (2011); Dokken B B et al., Glucagon-like peptide-1 (GLP-1), immediately prior to reperfusion, decreases neutrophil activation and reduces myocardial infarct size in rodents. *Horm Metab Res. May*; 43(5):300-5 (2011)).

Compositae plant of the present invention is preferably *Ligularia fischeri* (Ledeb). Turcz., *Lactuca india* L., *Dendranthema zawadskii* var. *latilobum* (Maxim.) Kitam.) or *Taraxacum platycarpum* Dahlst.

Brassicaceae plant of the present invention is preferably *Wasabia japonica* (Miq.) Matsum. Or *Brassica juncea* (L.) Czern. et coss.

Umbelliferae plant of the present invention is preferably *Pleurospermum camtschaticum* Hoffm., *Ligusticum tachiroei* (Franch. & Sav.) M.Hiroe & Constance or *Oenanthe javanica* (Blume) DC.

Labiatae plant of the present invention is preferably *Leonurus japonicus* Houtt. Or *Agastache rugosa* Kuntze.

Liliaceae plant of the present invention is preferably *Allium ochotense* Prokh or *Allium macrostemon* Bunge.

Amaranthaceae plant of the present invention is preferably *Amaranthus mangostanus* L.

In accordance with another aspect of the present invention, there is provided a method for screening an hTRPA1 antagonist, the method including:

(a) treating hTRPA1 with a candidate substance to be analyzed and a composition containing, as an active ingredient, coniferyl alcohol as an hTRPA1 agonist, or an extract of at least one selected from the group consisting of: (i) Compositae family plants consisting of *Ligularia fischeri* (Ledeb). Turcz., *Lactuca india* L., *Dendranthema zawadskii* var. *latilobum* (Maxim.) Kitam., and *Taraxacum platycarpum* Dahlst., (ii) Brassicaceae family plants consisting of *Wasabia japonica* (Miq.) Matsum. and *Brassica juncea* (L.) Czern. et coss, (iii) Umbelliferae family plants consisting of *Pleurospermum camtschaticum* Hoffm., *Ligusticum tachiroei* (Franch. & Sav.) M.Hiroe & Constance, and *Oenanthe javanica* (Blume) DC., (iv) Labiatae family plants consisting of *Leonurus japonicus* Houtt. and *Agastache rugosa* Kuntze, (v) Liliaceae family plants consisting of *Allium ochotense* Prokh. and *Allium macrostemon* Bunge, and (vi) *Amaranthus mangostanus* L.; and (b) measuring the activity of the hTRPA1, wherein the candidate substance is determined to be an hTRPA1 antagonist if the activity of the hTRPA1 is lower than that in a control group without the treatment with the candidate substance.

As validated in the following examples, coniferyl alcohol or the extract of the Compositae, Labiatae, Liliaceae, Amaranthaceae, Brassicaceae, or Umbelliferae family plant of the present invention induces hTRPA1 activation. Many documents disclose cases in which hTRPA1 activators are used for screening hTRPA1 antagonist. For example, U.S. Patent Application Publication Nos. 20070196866, 20080050750, 20090269280, and 20100273773 describe methods for screening hTRPA1 antagonist inhibiting or reducing activity of hTRPA1 that is activated by hTRPA1 activator.

According to the method of the present invention, first, coniferyl alcohol or an extract of the Compositae, Labiatae, Liliaceae, Amaranthaceae, Brassicaceae, or Umbelliferae family plant, as an hTRPA1 agonist, and a candidate substance to be analyzed are used to treat hTRPA1. The coniferyl alcohol or the extract of the Compositae, Labiatae, Liliaceae, Amaranthaceae, Brassicaceae, or Umbelliferae family plant activates hTRPA1, and a substance capable of inhibiting this activation is an hTRPA1 antagonist.

The hTRPA1 used herein is hTRPA1 itself or a cell expressing hTRPA1. Preferably, the hTRPA1 used herein is a cell stably expressing hTRPA1. The cell expressing hTRPA1 is preferably an animal cell, and examples thereof may include HEK293 cells, neuron, Chinese hamster ovary (CHO) cells, COS-7, HeLa, PC-12, and BAF, but are not limited thereto.

The candidate materials used in present invention include various materials. The candidate materials include chemical, protein, peptide, antibody, nucleic acid and a natural extract, but are not limited thereto. The candidate material analyzed by the screening method of the present invention is a single compound, a mixture of compounds (e.g., a natural extract or a cell or tissue culture), an antibody, or a peptide. The candidate material may be obtained from synthetic or natural compound libraries. These compound libraries are obtained by methods known in the art. The synthetic compound libraries are commercially available from Maybridge Chemical Co. (UK), Brandon Associates (USA), Microsource (USA), and Sigma-Aldrich (USA), and the natural compound libraries are commercially available from Pan Laboratories (USA) and MycoSearch (USA).

The test material may be obtained from various combinational library methods known in the art, for example, from a biological library method, a spatially addressable parallel solid phase or solution phase library method, a synthetic library method requiring deconvolution, a "one-bead one-compound" library method, and a synthetic library method using affinity chromatography selection. The synthetic methods of molecular libraries are disclosed in DeWitt et al., Proc. Natl. Acad. Sci. U.S.A. 90: 6909 (1993); Erb et al. Proc. Natl. Acad. Sci. U.S.A. 91: 11422 (1994); Zuckermann et al., J. Med. Chem. 37: 2678 (1994); Cho et al., Science 261: 1303 (1993); Carell et al., Angew. Chem. Int. Ed. Engl. 33: 2059 (1994); Carell et al., Angew. Chem. Int. Ed. Engl. 33: 2061; and Gallop et al., J. Med. Chem. 37: 1233 (1994).

In the method of the present invention, in step (b), the activity of the hTRPA1 may be determined in various manners.

Since the hTRPA1 is a cationic channel receptor, the cell membrane potential is changed by activation of hTRPA1. Therefore, the activity of hTRPA1 can be determined by measuring this change in the cell membrane potential. For example, the activity of hTRPA1 may be determined by using a fluorescent agent emitting fluorescence in response to a change in the cell membrane potential.

The representative cation flowing into cells by hTRPA1 activation is a calcium ion. Examples of a calcium-sensitive fluorescent agent used to measure the inflow of calcium ions into cells may include Fluo-3, Fluo-4, Fluo-5, Calcium Green, Calcium Orange, Calcium Yellow, Fura-2, Fura-4, Fura-5, Fura-6, Fura-FF, Fura Red, indo-1, indo-5, BTC (Molecular Probes), and FLIPR calcium 3 wash-free dye (Molecular Devices).

When the activity of hTRPA1 is measured by using a fluorescent agent, various fluorometers known in the art may be used.

As a result of measuring the activity of hTRPA1, when the activity of hTRPA1 is lower as compared with that in the control group without the treatment with the candidate substance, the candidate substance is determined to be an hTRPA1 antagonist. As used herein, the term "low" used while citing the term "control group" refers to that, when hTRPA1 activity is measured through a change in fluorescence by using a calcium-sensitive fluorescent agent, the relative fluorescence unit (RFU) is 2-100 times lower.

The hTRPA1 antagonist screened by the method of the present invention can be used as a pain medication (e.g., medications for chronic pain, acute pain, neuropathic pain, nociceptive pain, abdominal pain, nerve pain, etc.), an acute cerebral ischemia medication, an inflammatory medication, a neurodegenerative disease medication, a gastrointestinal disease medication, and a vomiting medication.

In accordance with another aspect of the present invention, there is provided a method for activating hTRPA1, the method including: treating isolated cells with a composition containing, as an active ingredient, coniferyl alcohol as an hTRPA1 agonist, or an extract of at least one selected from the group consisting of: (i) Compositae family plants consisting of *Ligularia fischeri* (Ledeb). Turcz., *Lactuca india* L., *Dendranthema zawadskii* var. *latilobum* (Maxim.) Kitam., and *Taraxacum platycarpum* Dahlst., (ii) Brassicaceae family plants consisting of *Wasabia japonica* (Miq.) Matsum. and *Brassica juncea* (L.) Czern. et coss, (iii) Umbelliferae family plants consisting of *Pleurospermum camtschaticum* Hoffm., *Ligusticum tachiroei* (Franch. & Sav.) M.Hiroe & Constance, and *Oenanthe javanica* (Blume) DC., (iv) Labiatae family plants consisting of *Leonurus japonicus* Houtt. and *Agastache rugosa* Kuntze, (v) Liliaceae family plants consisting of *Allium ochotense* Prokh. and *Allium macrostemon* Bunge, and (vi) *Amaranthus mangostanus* L.

Cells used herein include cells endogenously containing hTRPA1 gene or cells transformed with hTRPA1 gene.

According to a preferable embodiment of the present invention, the coniferyl alcohol used herein is contained in an extract of *Kalopanax pictus* sprouts or a fraction of *Kalopanax pictus* sprouts.

As used herein, the term "extract" used while citing the *Kalopanax pictus* sprouts, Compositae, Labiatae, Liliaceae, Amaranthaceae, Brassicaceae, or Umbelliferae family plant refers to the inclusion of an extraction product obtained by treating the *Kalopanax pictus* sprouts, Compositae, Labiatae, Liliaceae, Amaranthaceae, Brassicaceae, or Umbelliferae family plant with an extraction solvent, as well as such a formulated (e.g., pulverized) article that the *Kalopanax pictus* sprouts, Compositae, Labiatae, Liliaceae, Amaranthaceae, Brassicaceae, or Umbelliferae family plant itself can be administered to animals.

When the *Kalopanax pictus* sprouts, Compositae, Labiatae, Liliaceae, Amaranthaceae, Brassicaceae, or Umbelliferae plant extract used in the present composition is obtained by treating an extraction solvent to the plant, the extract may be prepared using various extraction solvents. Preferably, the extraction solvent includes polar and non-polar solvents. The suitable polar solvent includes (i) water, (ii) alcohols (preferably, methanol, ethanol, propanol, butanol, n-propanol, iso-propanol, n-butanol, 1-pentanol, 2-butoxyethanol or ethylene glycol), (iii) acetic acid, (iv) DMFO (dimethyl formamide) and (v) DMSO (dimethyl sulfoxide). The suitable non-polar solvent includes acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THF (Tetrahydrofuran).

More preferably, the extraction solvent used in this invention includes (a) water, (b) absolute or hydrous lower alcohol containing 1-4 carbon atoms (methanol, ethanol, propanol, butanol, etc.), (c) mixture of lower alcohol and water, (d) acetone, (e) ethyl acetate, (f) chloroform, (g) butyl acetate, (h) 1,3-butyleneglycol, (i) hexane and (j) diethylether. The extraction solvent used in this invention is more preferably water or ethanol, most preferably ethanol.

As used herein, the term "fraction" used while citing the *Kalopanax pictus* sprouts, Compositae, Labiatae, Liliaceae, Amaranthaceae, Brassicaceae, or Umbelliferae family plant refers to the enrichment fraction of hTRPA1 activating component obtained by treating the *Kalopanax pictus* sprouts, Compositae, Labiatae, Liliaceae, Amaranthaceae, Brassicaceae, or Umbelliferae family plant with an additional extraction solvent. When the *Kalopanax pictus* sprouts, Compositae, Labiatae, Liliaceae, Amaranthaceae, Brassicaceae, or Umbelliferae plant fraction used in the present composition is obtained by treating an extraction solvent to the plant, the extract may be prepared using various extraction solvents. Preferably, the extraction solvent includes polar and non-polar solvents. The suitable polar solvent includes (i) water, (ii) alcohols (preferably, methanol, ethanol, propanol, butanol, n-propanol, iso-propanol, n-butanol, 1-pentanol, 2-butoxyethanol or ethylene glycol), (iii) acetic acid, (iv) DMFO (dimethyl formamide) and (v) DMSO (dimethyl sulfoxide). The suitable non-polar solvent includes acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THF (Tetrahydrofuran).

More preferably, the extraction solvent used in this invention includes (a) absolute or hydrous lower alcohol containing 1-4 carbon atoms (methanol, ethanol, propanol, butanol, normal-propanol, iso-propanol and normal-butanol, etc.), (b) mixture of lower alcohol and water, (c) acetone, (d) ethyl acetate, (e) chloroform, (f) 1,3-butyleneglycol, (g) hexane, (h) diethylether or (i) butylacetate. The fraction used in this invention is more preferably water fraction obtained by treating the ethanol extract of the *Kalopanax pictus* sprouts, Compositae, Labiatae, Liliaceae, Amaranthaceae, Brassicaceae, or Umbelliferae family plant with ethyl acetate.

The plant extract or solvent fraction used in present invention not only the resultant of extraction using the extraction solvent described above but also the resultant of additional purifications. For instance, it could be appreciated that active fractions obtained using a variety of additional purification methods such as an ultrafiltration with defined molecular weight cut-off value and various chromatography (designed for purification dependent upon size, charge, hydrophobicity and affinity) are included in the present extracts.

The plant extract or fraction used in present invention may be powdered through additional processes such as lyophilization and spray drying.

According to a preferable embodiment of the present invention, the coniferyl alcohol causes lacrimation by activating hTRPA1. Therefore, according to still another aspect of the present invention, the present invention provides a lacrimatory composition containing coniferyl alcohol as an active ingredient.

Since the connection between hTRPA1 activation and lacrimatory characteristics is described in many documents, the following example data suggesting that coniferyl alcohol strongly activates hTRPA1 sufficiently support a use of coniferyl alcohol as a lacrimatory agent. The connection between hTRPA1 activation and lacrimatory characteristics is clearly described in Brone B et al., Tear gasses CN, CR, and CS are potent activators of the human TRPA1 receptor. Toxicol. Appl. Pharmacol. 231(2): 150-6 (2008); U.S. Patent Application Publication No. 20100273773; and U.S. Patent Application Publication No. 20110144137.

The present composition may be prepared to a pharmaceutical composition.

When the composition of the present disclosure is prepared as a pharmaceutical composition, the pharmaceutical composition of the present disclosure may comprise a pharmaceutically acceptable carrier.

The pharmaceutical composition may contain a pharmaceutically acceptable carrier. In the pharmaceutical compositions of this invention, the pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in Remington's Pharmaceutical Sciences (19th ed., 1995), which is incorporated herein by reference.

The pharmaceutical composition of this invention may be administered orally or parenterally, preferably orally.

A suitable dose of the pharmaceutical composition of the present invention may vary depending on pharmaceutical formulation methods, administration methods, the patient's age, body weight, sex, severity of diseases, diet, administration time, administration route, an excretion rate and sensitivity for a used pharmaceutical composition. Physicians of ordinary skill in the art can determine an effective amount of the pharmaceutical composition for desired treatment. Generally, the pharmaceutical composition of the present invention may be administered with a daily dose of 0.001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. The formulation may be in the form of a solution in oily or aqueous medium, a suspension, a syrup, a emulsion, an extract, an elixir, a powder, a granule, a tablet or a capsule, and may further include a dispersant or stabilizer.

The present composition may be provided in a food composition.

When the composition of the present disclosure is prepared as a food composition, the food composition of the present disclosure may comprise, in addition to a coniferyl alcohol or an extract of the Compositae, Labiatae, Liliaceae, Amaranthaceae, Brassicaceae, or Umbelliferae of the present disclosure as the active ingredient, ingredients commonly added for preparation of food. For example, proteins, carbohydrates, fats, nutrients, seasoning or flavors may be added. The carbohydrate may be, for example, a sugar such as a monosaccharide, e.g., glucose, fructose, etc.; a disaccharide, e.g., maltose, sucrose, oligosaccharide, etc.; and a polysaccharide, e.g., dextrin, cyclodextrin, etc. and a sugar alcohol such as xylitol, sorbitol, erythritol, etc. The flavor may be a natural flavor [thaumatin, stevia extract (e.g., rebaudioside A, glycyrrhizin, etc.]) or a synthetic flavor (saccharin, aspartame, etc.). For example, when the food composition of the present disclosure is prepared as a drink, it may further comprise, in addition to the plant extract of the present disclosure, citric acid, liquefied fructose, sucrose, glucose, acetic acid, malic acid, fruit juices, Eucommia ulmoides extracts, jujube extracts, licorice extracts or the like.

Advantageous Effects

Features and advantages of the present invention are summarized as follows:

(a) The present invention provides various uses associated with an increase in hTRPA1 activity in a composition containing coniferyl alcohol or an extract of at least one plant selected from the group consisting of the Compositae, Labiatae, Liliaceae, Amaranthaceae, Brassicaceae, and Umbelliferae family plants, for example, uses as a pungent flavor agent, an antiobesity agent, and for screening an hTRPA1 antagonist.

(b) The coniferyl alcohol or an extract of the Compositae, Labiatae, Liliaceae, Amaranthaceae, Brassicaceae, or Umbelliferae family plant of the present invention provides various uses associated with hTRPA1 activation, is a natural compound and thus has relatively few side effects to the human body, and has high industrial applicability.

(c) The coniferyl alcohol or an extract of the Compositae, Labiatae, Liliaceae, Amaranthaceae, Brassicaceae, or Umbelliferae family plant of the present invention is a material for novel medication or food, which is helpful to maintain homeostasis in the body in association with hTRPA1 activation, and is useful for the screening of hTRPA1 antagonists.

BRIEF DESCRIPTION OF THE DRAWINGS

FIG. 21A and FIG. 21B illustrate procedures for obtaining KPsx-DW and KPsx-EA from KPsx and KPsEtx-DW and KPsEtx-EA from KPsEtx, respectively.

Hereinafter, the present invention will be described in more detail through examples. These examples are only for illustrating the present invention more specifically, and it will be apparent to those skilled in the art that the scope of the present invention is not limited by these examples.

EXAMPLES

Materials and Method
1. Materials
1-1. Compositae Family Plants

For *Ligularia fischeri* (Ledeb). Turcz., *Lactuca india* L., *Dendranthema zawadskii* var. *latilobum* (Maxim.) Kitam., and *Taraxacum platycarpum* Dahlst., plants growing naturally in the country or those proliferating in the Korea Botanic Garden (Pyeongchang, Gangwon-do) from March to August, 2010 were used.

1-2. Labiatae Family Plants

For *Leonurus japonicus* Houtt. and *Agastache rugosa* (Fisch. & Mey.) Kuntze, plants growing naturally in the country or those proliferating in the Korea Botanic Garden (Pyeongchang, Gangwon-do) from March to August, 2010 were used.

1-3. Liliaceae Family Plants

For *Allium ochotense* Prokh. and *Allium macrostemon* Bunge, plants growing naturally in the country or those proliferating in the Hantaek Botanical Garden (Yongin, Gyeonggi-do) from March to August, 2010 were used.

1-4. Amaranthaceae Family Plants

For *Amaranthus mangostanus* L., those proliferating in the Hantaek Botanical Garden (Yongin, Gyeonggi-do) from March to August, 2010 were used.

1-5. Brassicaceae Family Plants

For *Wasabia japonica* (Miq.) Matsum. and *Brassica juncea* (L.) Czern. et coss, plants growing naturally in the country or those proliferating in the Korea Botanic Garden (Pyeongchang, Gangwon-do) from March to August, 2010 were used.

1-6. Umbelliferae Family Plants

For *Pleurospermum camtschaticum* Hoffm., *Ligusticum tachiroei* (Franch. & Sav.) M.Hiroe & Constance, and *Oenanthe javanica* (Blume) DC., plants growing naturally in the country or those proliferating in the Korea Botanic Garden (Pyeongchang, Gangwon-do) from March to August, 2010 were used.

1-7. *Kalopanax pictus* Sprouts

Among Korean aromatic plants which cause pungent chemosensation, such as spicy, tingle, and tangy tastes, sprouts of *Kalopanax pictus* (English name: Carstor Araila) (*Kalopanax pictus* shoots, hereinafter, referred to as KPs) that have been widely used for food, such as wild greens and spices were used. Coniferyl alcohol (Chemical Formula 1) was purchased from Wako Pure Chem. Ind. (Osaka, Japan).

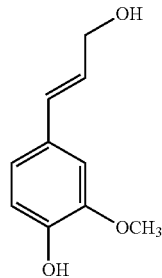

Chemical Formula 1

2. Establishment of Conditions Appropriate for Preparation of Extracts

Figure 1:
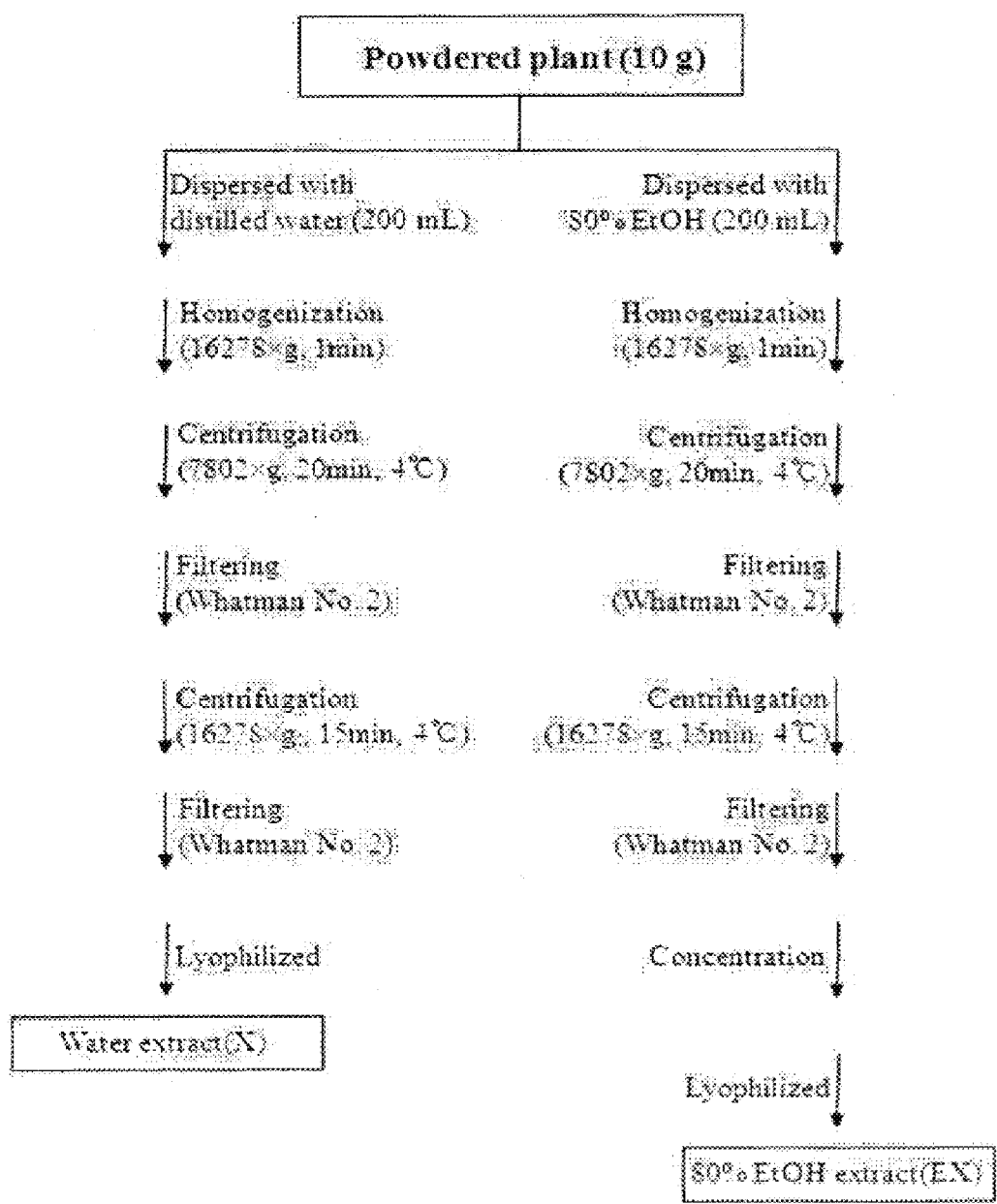
FIG. 1 illustrates a procedure for preparing a water-soluble crude extract (X) and an alcoholic crude extract (EX) of a plant.

The whole plant for each sample was collected from a mountain region, washed, lyophilized, crushed, and stored at −80° C. for the use. A water-soluble crude extract and an alcoholic crude extract of each sample were prepared according to the extracting method shown in FIG. 1. The water-soluble crude extract was obtained by dispersing 10 g of powdered plant with 200 mL of distilled water added thereto, followed by homogenization at 16,278×g for 1 minute, centrifugation at 7,802×g for 20 minutes at 4° C., filtering, centrifugation at 16,278×g for 15 minutes, filtering, and lyophilization. The alcoholic crude extract was obtained by dispersing 10 g of powdered plant with 200 mL of 80% ethanol added thereto, followed by homogenization at 16,278×g for 1 minute, centrifugation at 7,802×g for 20 minutes at 4° C., filtering, centrifugation at 16,278×g for 15 minutes, filtering, and lyophilization. The water-soluble crude extract and the alcoholic crude extract were dried under reduced pressure and lyophilized, and then stored at 4° C. before being used for experiments.

Figure 21:
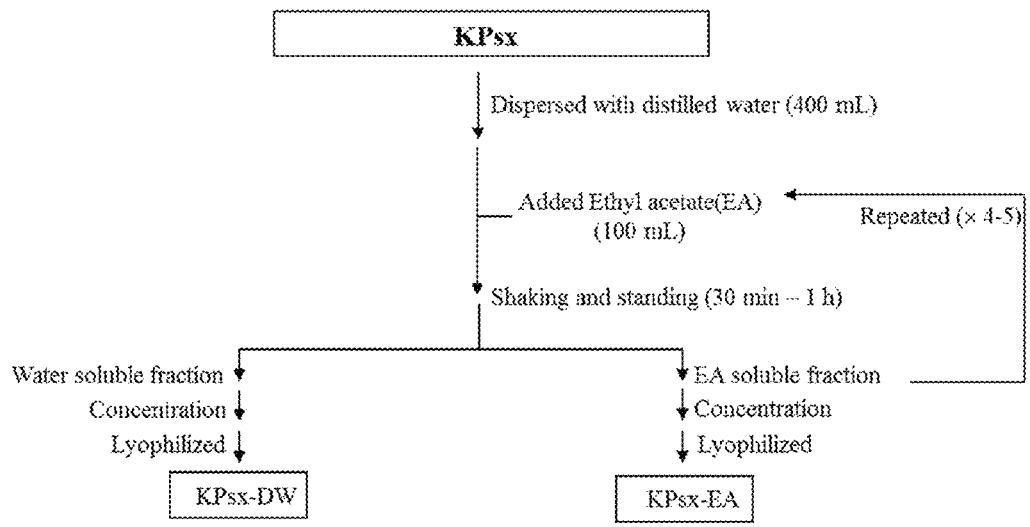
FIG. 21 illustrates a fractionating procedure for obtaining a water fraction (DW) and an acetic acid fraction (EA) from a crude extract.
Figure 21:
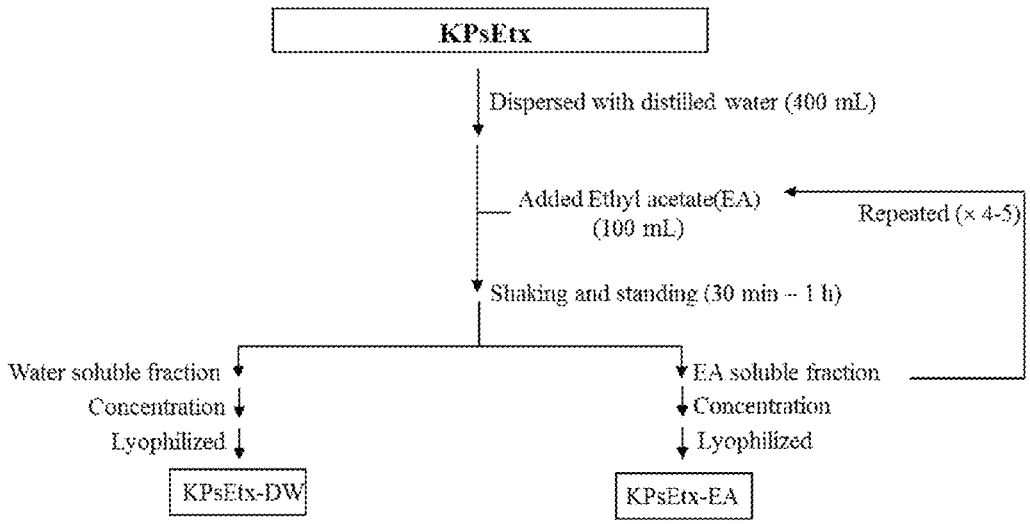

With respect to the *Kalopanax pictus* sprouts, according to the method shown in FIG. 21, KPsx and KPsEtx were extracted from the active material KPs, and then subjected to fractionation, thereby preparing water-soluble fractions (KPsx-DW and KPsEtx-DW) and ethyl acetate (EA)-soluble fractions (KPsx-EA and KPsEtx-EA).

3. HPLC Analysis of Active Ingredients of KPs Extracts

Figure 22:
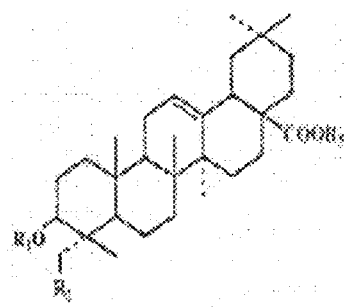
FIG. 22 shows chemical structures of a KPs standard material and a phenolic compound. A left panel shows a chemical structure of saponin-based compound, which represents Kalopanax saponin A ($R_1$=α-L-Rha-(1-2)-α-L-Ara, $R_2$=OH, $R_3$=H) and Kalopanax saponin B ($R_1$=α-L-Rha-(1-2)-α-L-Ara, $R_2$=OH, $R_3$=α-L-Rha-(1-4)-β-D-Glc-(1-6)-β-D-Glc), depending on the R group. A light panel shows a chemical structure of phenolic compound, and A represents a chemical structure of syringin ($R_1$=$CH_2OH$, $R_2$=OMe, $R_3$=H) or coniferyl alcohol ($R_1$=$CH_2OH$, $R_2$=H, $R_3$=Api) and B represents a chemical structure of protocatechuic acid ($R_1$=—H, $R_2$=H, $R_3$=Me), chlrogenic acid$^B$ ($R_1$=—H, $R_2$=OMe, $R_3$=Glc), or methyl syringate ($R_1$=-Me, $R_2$=OMe, $R_3$=Rha).
Figure 22:
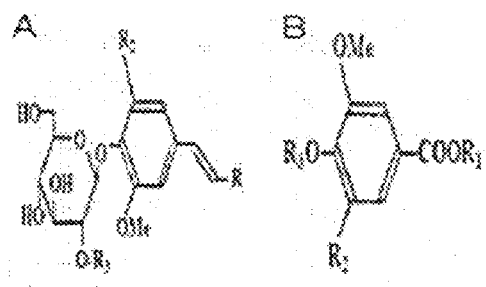
Figure 23:
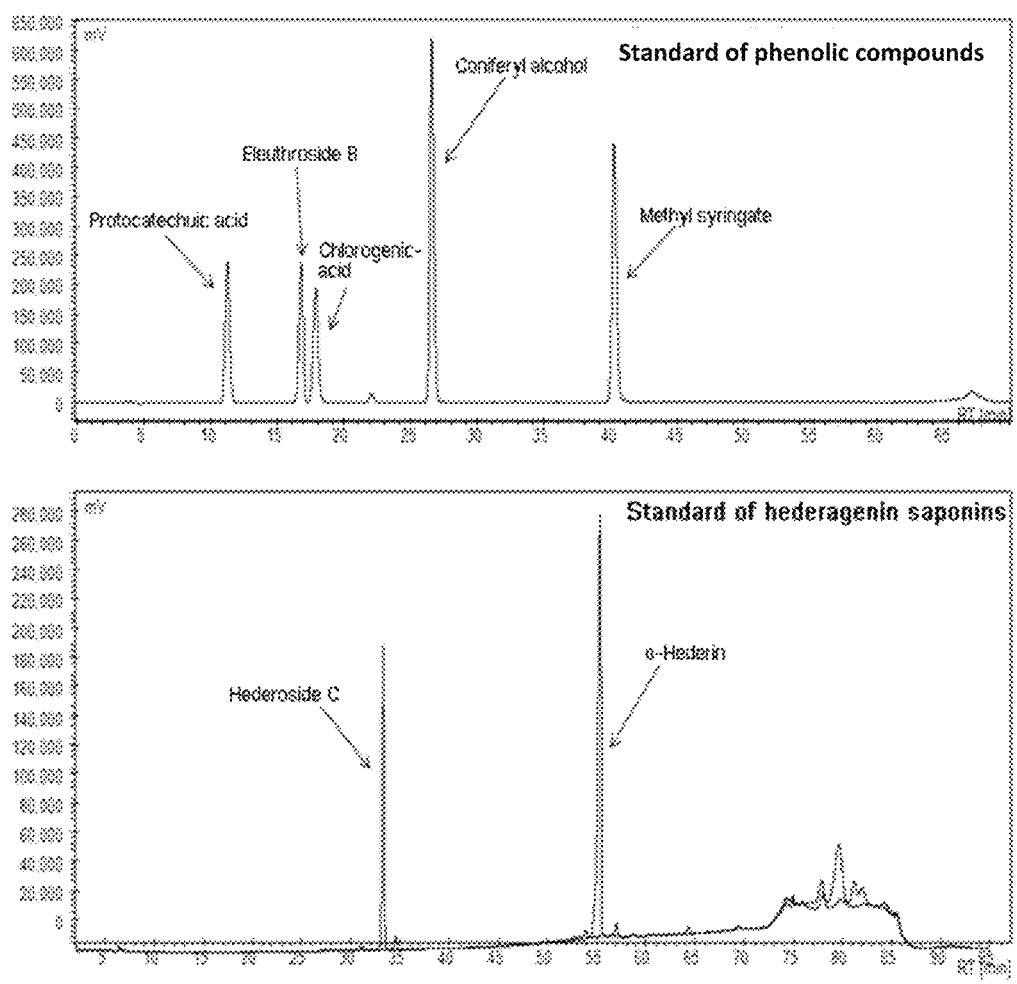
FIG. 23 shows HPLC standard chromatograms of the saponin-based compound and phenolic compound.
Figure 24:
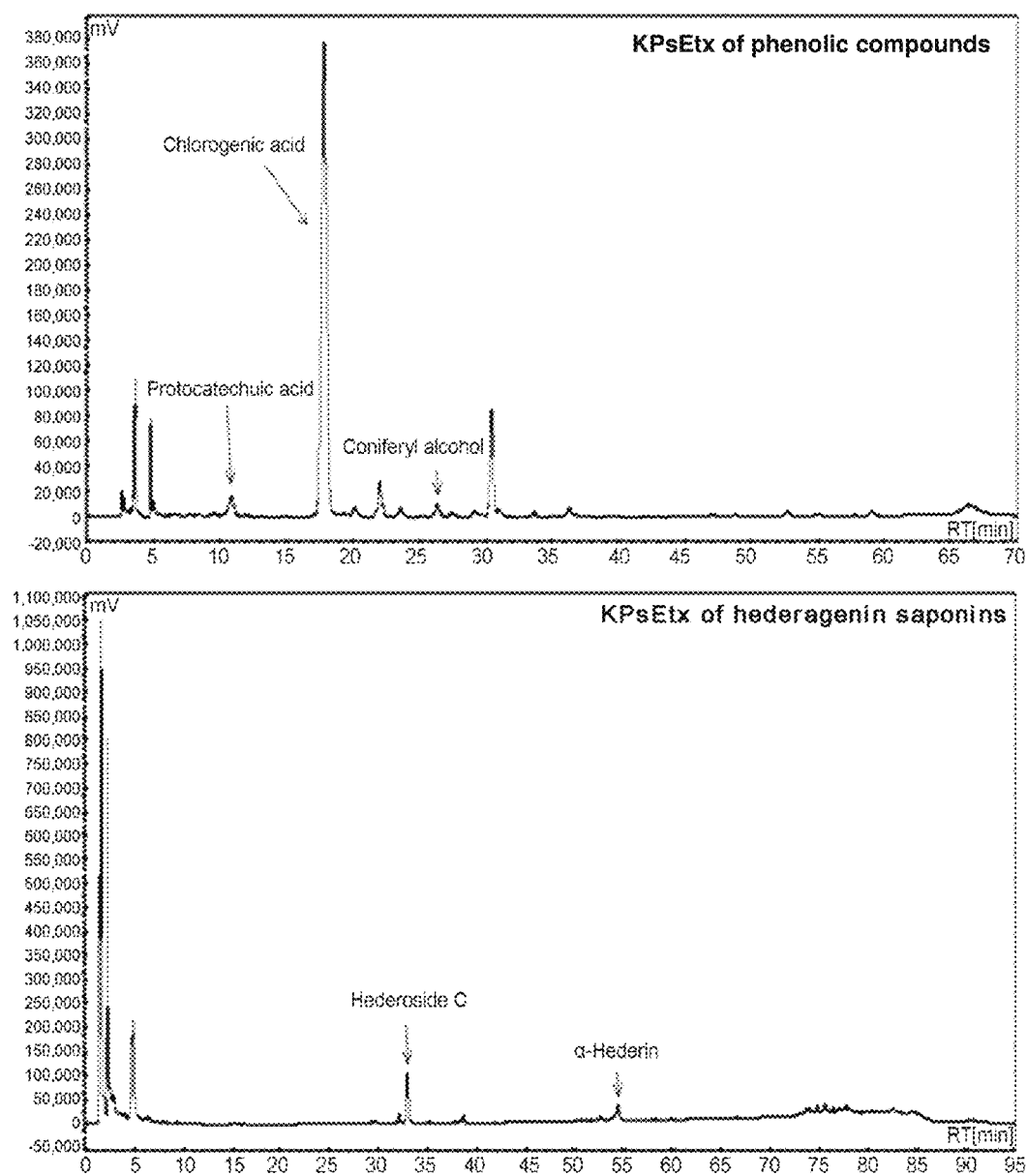
FIG. 24 shows chromatogram of KPsEx.
Figure 25:
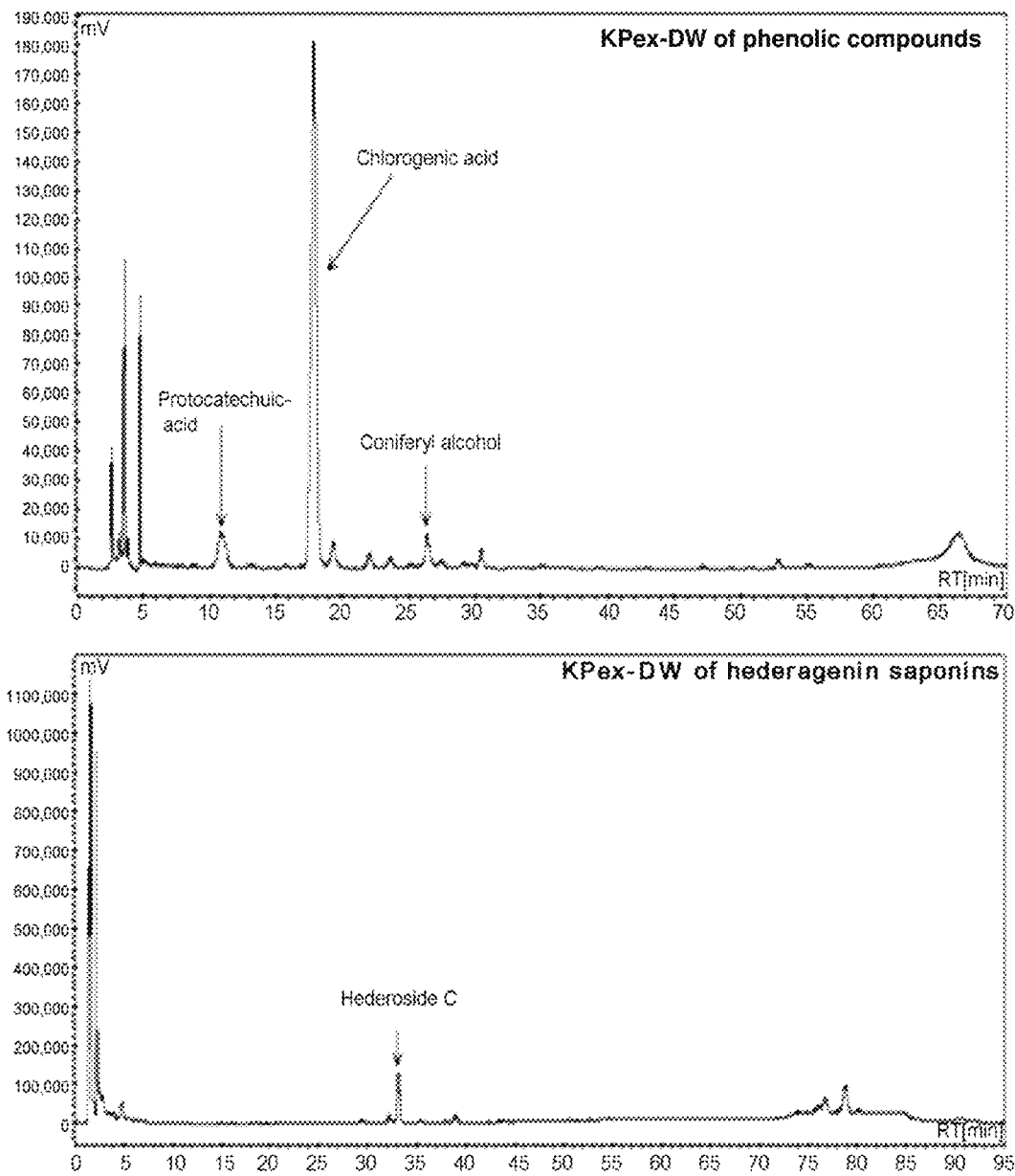
FIG. 25 shows chromatogram of KPsEtx-DW.
Figure 26:
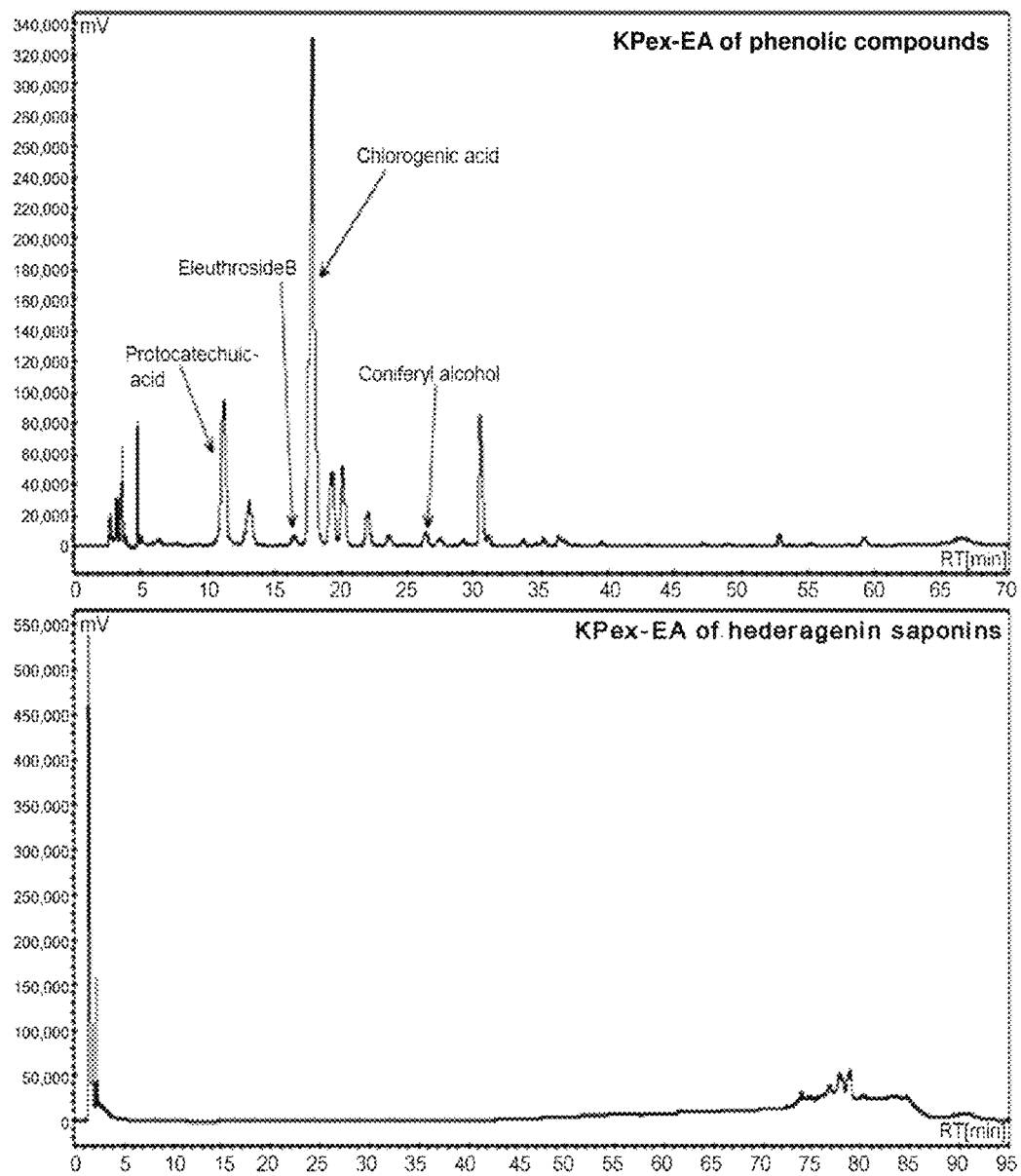
FIG. 26 shows chromatogram of KPsEtx-EA.

Six KPs fractions (KPsx, KPsEtx, KPsx-DW, KPsEtx-DW, KPsx-EA, and KPsEtx-EA) were subjected to HPLC analysis using standard materials, such as Kalopanaxsaponin A (α-hederin) and Kalopanaxsaponin B (hederacoside C), and phenolic compounds, such as syringin, methyl syringate, chlorogenic acid, coniferyl alcohol, and protocatechuic acid (FIG. 22).

For the analysis of phenolic ingredients, a Bondpack C18 column (Waters, USA, 10, 300×3.9 mm) was used, and elution was carried out at a flow rate of 0.8 ml/min using, as a mobile phase, 20 acetic acid in distilled water (solvent A) and 0.5% acetic acid in 50% acetonitrile (solvent B). The gradient of solvent B was 10% at the initial time to 80% after 60 minutes. The temperature of the column was maintained at 40° C., and the detection of the sample was monitored at 280 nm.

For the analysis of saponin-based ingredients, a Bondpack C18 column (Waters, USA, 10, 300×3.9 mm) was used, and elution was carried out using, as a mobile phase, distilled water (solvent A) and acetonitrile (solvent B). The gradient of solvent A was 80% at the initial time to 35% after 70 minutes. The flow rate of elution was 1.6 ml/min, the temperature of the column was maintained at 25° C., and the detection of the sample was monitored at 203 nm.

4. Stable Cell Line Expression

The hTRPA1-expressing gene (coding region) was cloned according to the manufacturer's protocol for the pcDNA5/FRT Complete System (Invitrogen). In order to verify whether the hTRPA1 gene was accurately inserted into the vector, sequencing was carried out using the ABI 130 or 310 DNA generatic analyzer (Applied Biosystems), and the constructed vector and Pog44 were transduced into Flin-in 293 cells using Lipofectamine 2000 (Invitrogen). After 24 hours, the cells were optionally treated with 100 μg/ml of hygromycin-B (Invitrogen), following by further culturing for 2-3 weeks. Then, only antibiotic-resistant cells were collected, and used for measuring cellular responses of hTRPA1, followed by repeated culturing. The cells were cultured in Dulbecco's modified Eagle's medium (DMEM) supplemented with 10% fetal bovine serum.

5. Evaluation of hTRPA1 Action Using $Ca^{2+}$ Imaging

The $Ca^{2+}$ imaging was conducted to measure hTRPA1 activation. Fura-2/AM (Molecular Probes, USA) was used as a marker for measuring the change in the intracellular calcium concentration. At 20-26 hours before the analysis, cell lines stably expressing hTRPA1 were dispensed in a 96-well plate. The cells were cultured in a solution added with Fura-2/AM (5 μM) at 27° C. for 30 minutes. The cells were washed with an assay buffer (140 mM NaCl, 10 mM HEPES, 2 mM $CaCl_2.2H_2O$, 2 mM EGTA, 1 mM $MgCl_2.6H_2O$, 10 mM glucose, and 5 mM KCl), added with 100 μL of the assay buffer, and left at room temperature for 15 minutes. The Fura-2/AM-loaded cells were placed on a microscope, and the fluorescence absorbance was measured between 340 nm and 380 nm. The images were recorded at 3-sec intervals, and the change in the intracellular calcium concentration was analyzed using MetalFluor software (Molecular Devices, Sunnyvale, Calif., USA).

6. Measurement of Intracellular $Ca^{2+}$ Concentration Using Cell-Based Analysis The intercellular $Ca^{2+}$ concentration was measured by using FlexStation™ (Molecular Devices, Sunnyvale, Calif., USA). Cells were dispensed at 24 hours before the analysis, and treated with 5 μM Fluo-4-AM (Molecular Probes, Eugene, Oreg., USA) as a marker for measuring the change in the intracellular calcium concentration, followed by reaction at 27° C. for 30 minutes. After that, the cells were washed with an assay buffer (140 mM NaCl, 10 mM HEPES, 2 mM $CaCl_{22}H_2O$, 2 mM EGTA, 1 mM $MgCl_{26}H_{2o}$, 10 mM glucose, and 5 mM KCl), added with 100 μL of the assay buffer, and left at room temperature for 15 minutes. Then, each of extracts and compositions was treated and used to measure fluorescence absorbance at 486 nm (F486) and 516 nm (F516). The change in intercellular calcium concentration was represented as A relative fluorescent unit (RFU), and was analyzed by using the Softmax software (Molecular devices, USA).

7. Sensory Test

The sensory test was conducted for the pungent flavor due to coniferyl alcohol. A solution of 1 μM coniferyl alcohol was used, and the sensitivity of the pungent taste was marked in a 15-point scale (n=6).

8. Lacrimation Test

The lacrimation test was conducted on the coniferyl alcohol. A solution of 1 μM coniferyl alcohol was used, and experiment participants were asked to write down their feeling when the solution was sprayed onto their eyes.

9. Analysis of Effect on GLP-1 Secretion (Analysis of Anti-Diabetic and Anti-Obesity Efficacies)

Glucagon-like peptide-1 (GLP-1), which is the hormone secreted from the gut, is involved in an anti-diabetic action by amplifying glucose-stimulated insulin secretion and suppressing the beta-cell death. GLP-1 is also involved in an anti-obesity action by decreasing the rate of gastric emptying and suppressing the appetite. Therefore, a GLP-1 secreting material can be expected to have anti-diabetic and anti-obesity effects.

10. Cell Culture

The human-derived cell line NCI-H716 cells were purchased from the American Type Culture Collection (ATCC, Manassas, Va.). This cell line corresponds to suspension cells isolated from the large-intestinal Adenocarcinoma of a 33-year-old Caucasian adult male, and has been known as a cell line that mainly secrets GLP-1. For the maintenance of proliferation and culture of the cell line, the cells were cultured in RPMI 1640 medium supplemented with 10% fetal bovine serum (FBS), 2 mM L-glutamine, 100 IU/ml penicillin, and 100 μg/ml streptomycin, and for the adherence and differentiation of cells, the Matrigel matrix (Becton Dickinson and Co., Bedford, Mass.) was coated on plates and the cells were cultured in high-glucose DMEM supplemented with 10% FBS, 2 mm L-glutamine, 100 IU/ml penicillin, and 100 μg/ml streptomycin.

11. GLP-1 section effect in NCI-H716 cells

The NCI-H716 cell line was cultured at $2 \times 10^5$ cells/mL in a 96-well culture plate coated with Matrigel for 3 days. On the day of the experiment, the cells were washed with 1× phosphated buffered saline (PBS). For the control group, Krebs-Ringer bicarbonate buffer (KRB, 128.8 mmol/l NaCl, 4.8 mmol/l KCl, 1.2 mmol/l $KH_2PO_4$, 1.2 mmol/l $MgSO_4$, 2.5 mmol/l $CaCl_2$, 5 mmol/l $NaHCO_3$, and 10 mmol/l HEPES, 0.2% BSA, pH 7.4) was used. For the analysis, the samples of different concentrations were added thereto, followed by incubation at 37° C. for 1 hour. After the incubation, the supernatant was taken (100 μL) for GLP-1 analysis, and analyzed by using the GLP-1 active ELISA kit (EGLP-35K, Millipore) according to the manufacturer's manual. The concentration of GLP-1 was calculated based on the supplied GLP-1 standard material (pmol).

Results

1. Selection of Compositae Family Plants

It has been already reported that food ingredients having pungent flavor characteristics, such as, garlic, pepper, and the like, which are representative spices in Korean foods, activate transient receptor potential (TRP) ion channel-based receptors. It has been so far reported that the materials capable of stimulating TRPA1 are isothiocyanate as a main ingredient of mustard or horseradish, acrolein used as lacrimatory gas, cinnamaldehyde as an ingredient of cinnamon oil, tetrahydrocannabiol as an ingredient of marijuana, bradykinin, and the like. Herein, it was thought that there are various materials exhibiting pungent flavor characteristics amongst plants such as wild greens which have been used for food for a long time in Korea, and the materials for activating TRP-based receptors were searched for based on the Compositae family plants in the wild greens used for food.

Among Korean aromatic plants which cause pungent chemosensation, such as spicy, tingle, and tangy tastes, *Ligularia fischeri* (Ledeb). Turcz., *Lactuca india* L., *Dendranthema zawadskii* var. *latilobum* (Maxim.) Kitam., and *Taraxacum platycarpum* Dahlst. (Table 1) were selected for the Compositae family plants widely used for food, such as wild greens, spices, and the like.

TABLE 1

Selected Compositae family plants

| — | Abbreviation | English name | Binomial name | Part used | Family | Collection place |
|---|---|---|---|---|---|---|
| 1 | LF | Gomchwi | *Ligularia fischeri* (Ledeb.) Turcz. | Leaves | Compositae | Gyeonggi-do |
| 2 | LI | *Lactuca indica* | *Lactuca indica* L. | Leaves | Compositae | Ulleungdo island |
| 3 | DZ | Siberian chrysanthemum | *Dendranthema zawadskii* var. *latilobum* (Maxim.) Kitam. | The whole | Compositae | Chungcheong-do |
| 4 | TP | Dandleion | *Taraxacum platycarpum* Dahlst. | Stems and Leaves | Compositae | Jeollanam-do |

2. Selection of Labiatae, Liliaceae, and Amaranthaceae Family Plants

Among Korean aromatic plants which cause pungent chemosensation, such as spicy, tingle, and tangy tastes, *Leonurus japonicus* Houtt. and *Agastache rugosa* (Fisch. & Mey.) Kuntze (Table 2), *Allium ochotense* Prokh. and *Allium macrostemon* Bunge (Table 3), and *Amaranthus mangostanus* L. (Table 4) were, respectively, selected for the Labiatae family plants, the Liliaceae family plants, and the Amaranthaceae family plant, which have been widely used for food, such as wild greens, spices, and the like.

TABLE 2

Selected Labiatae family plants

| — | Abbreviation | English name | Binomial name | Part used | Family | Collection place |
|---|---|---|---|---|---|---|
| 1 | LJ | Siberian Motherwort | *Leonurus japonicus* Houtt. | Stems and Leaves | Labiatae | Chungcheong-do |
| 2 | AR | Wrinkled Giant Hyssop | *Agastache rugosa* (Fisch. & Mey.) Kuntze | Stems and Leaves | Labiatae | Chungcheong-do |

TABLE 3

Selected Liliaceae family plants

| — | Abbreviation | English name | Binomial name | Part used | Family | Collection place |
|---|---|---|---|---|---|---|
| 1 | AO | Lily leek | *Allium ochotense* Prokh. | Stems and Leaves | Liliaceae | Ulleungdo island |
| 2 | AIM | Uniflower Onion | *Allium monanthum* Maxim. | The whole | Liliaceae | Gyeonggi-do |

TABLE 4

Selected Amaranthaceae family plants

| — | Abbreviation | English name | Binomial name | Part used | Family | Collection place |
|---|---|---|---|---|---|---|
| 1 | AM | Amaranth | *Amaranthus mangostanus* L. | Leaves | Amaranthaceae | Gyeonggi-do |

3. Selection of Brassicaceae and Umbelliferae Family Plants

Among Korean aromatic plants which cause pungent chemosensation, such as spicy, tingle, and tangy tastes, *Wasabia japonica* (Miq.) Matsum. and *Brassica juncea* (L.) Czern. et coss (Table 5) and *Pleurospermum camtschaticum* Hoffm., *Ligusticum tachiroei* (Franch. & Sav.) M.Hiroe & Constance, and *Oenanthe javanica* (Blume) DC. (Table 6) were, respectively, selected for the Brassicaceae family plants and the Umbelliferae family plants, which have been widely used for food, such as wild greens, spices, and the like.

TABLE 5

Selected Brassicaceae family plants

| — | Abbreviation | English name | Binomial name | Part used | Family | Collection place |
|---|---|---|---|---|---|---|
| 1 | WJ | Horseradish leaf | *Wasabia japonica* (Miq.) Matsum. | Leaves | Brassicaceae | Gangwon-do |
| 2 | BJ | Brown mustard | *Brassica juncea* (L.) Czern. et coss | Leaves | Brassicaceae | Jeollanam-do |

TABLE 6

Selected Umbelliferae family plants

| — | Abbreviation | English name | Binomial name | Part used | Family | Collection place |
|---|---|---|---|---|---|---|
| 1 | PC | Kamchatka Pleurospermum | *Pleurospermum camtschaticum* Hoffm. | Stems and Leaves | Umbelliferae | Gangwon-do |
| 2 | LT | Gaehoehyang | *Ligusticum tachiroei* (Franch. & Sav.) M. Hiroe & Constance | The whole | Umbelliferae | Gangwon-do |
| 3 | OJ | Javan Waterdropwort | *Oenanthe javanica* (Blume) DC. | Stems and Leaves | Umbelliferae | Chungcheong-do |

4. Confirmation of Stable Sell Line Expression

Figure 2:
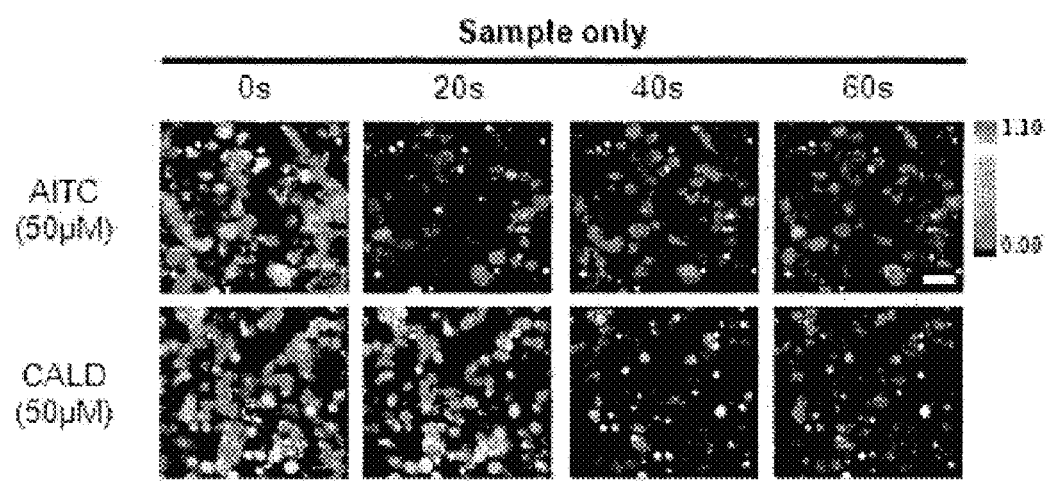
FIG. 2 illustrates experimental results verifying the response of hTRPA1 channel-expressing cells to allyl isothiocyanate (AITC) and cinnamaldehyde (CALD), which are TRPA1 channel agonists, through $Ca^{2+}$ imaging analysis.

In order to verify hTRPA activity, the hTRPA1 stably expressing cell line was established, and in order to verify the receptor-stimulating activity of the hTRPA1 stably expressing cell line, the cells were treated with AITC and CALD as agonists thereof. As a result, it can be confirmed that the calcium was released for 50 μM AITC and CALD and the calcium release was increased according to the response time, and thus the cells used in the present research were suitable for research (FIG. 2).

5. Extracts of Compositae Family Plants

Figure 3A:
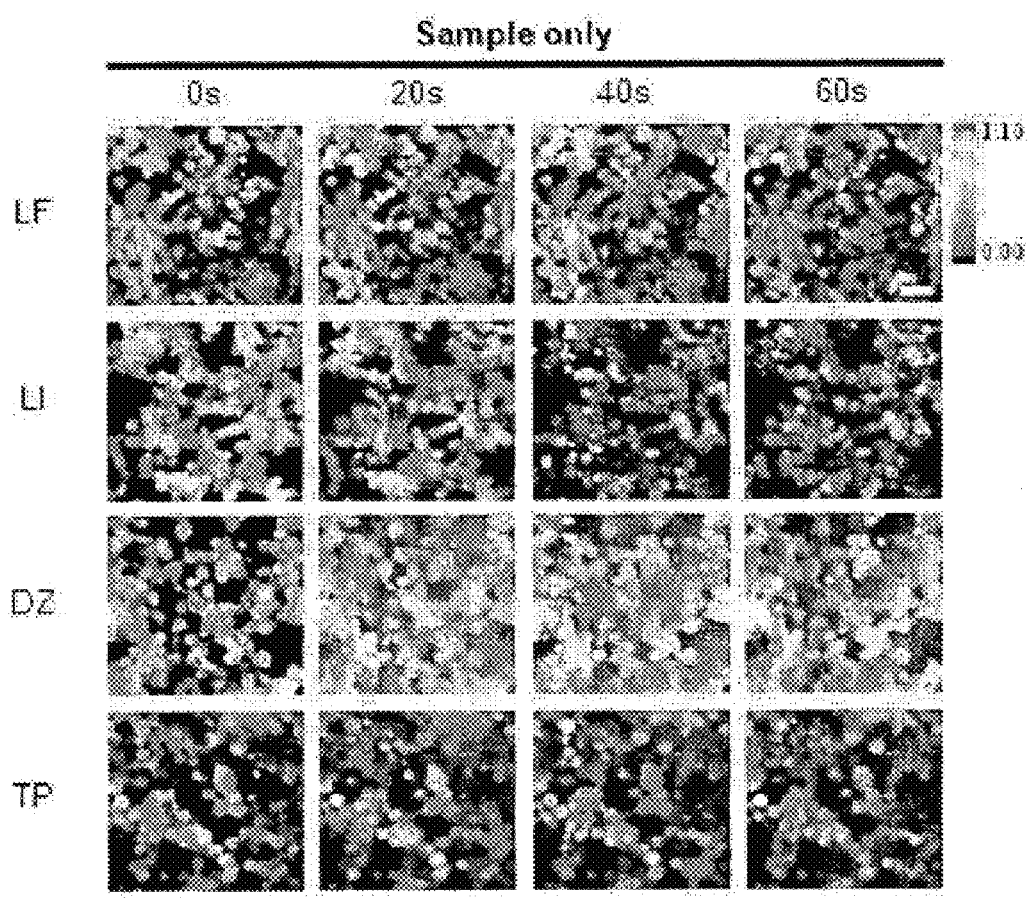
FIG. 3 illustrates images showing the response of hTRPA1 channel-expressing cells to extracts of 4 species of the family Compositae through $Ca^{2+}$ imaging analysis. RR represents the treatment with the TRP channel blocker, ruthenium red (RR), and HC-030031 represents the treatment with TRPA1-specific antagonist HC-030031.
Figure 3B:
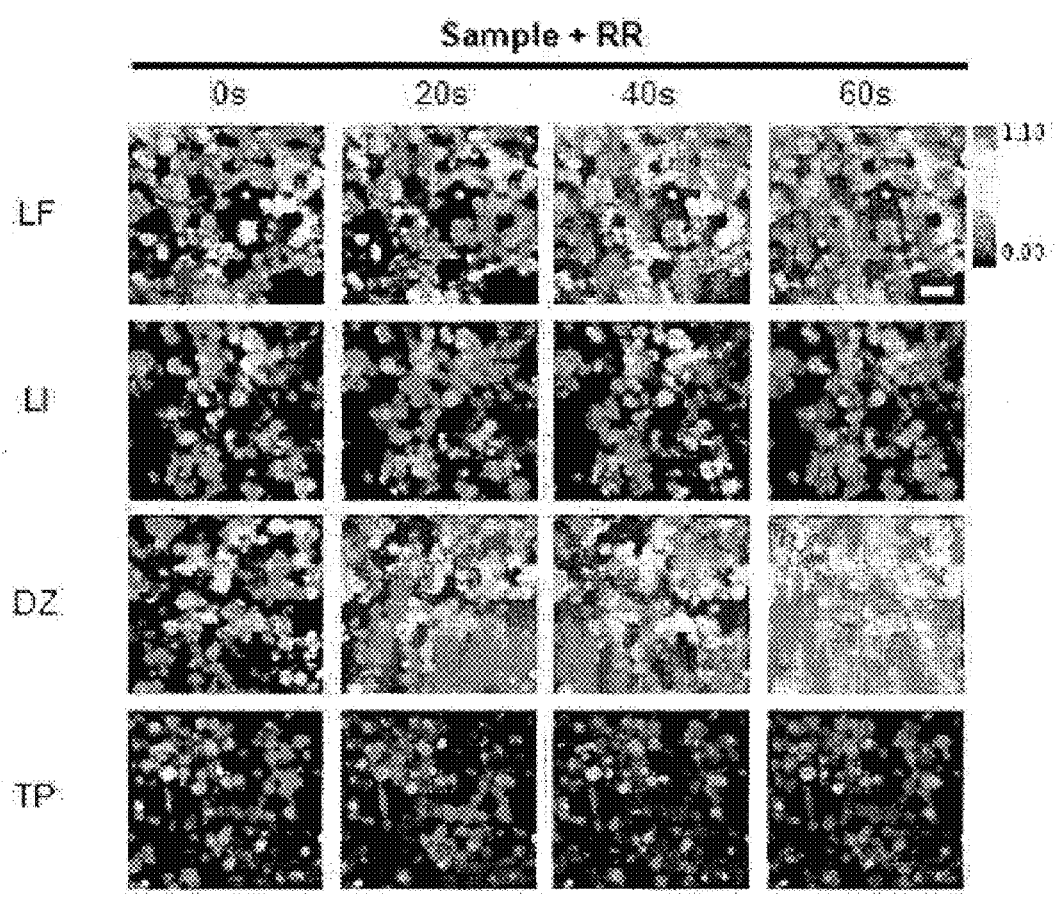
Figure 3C:
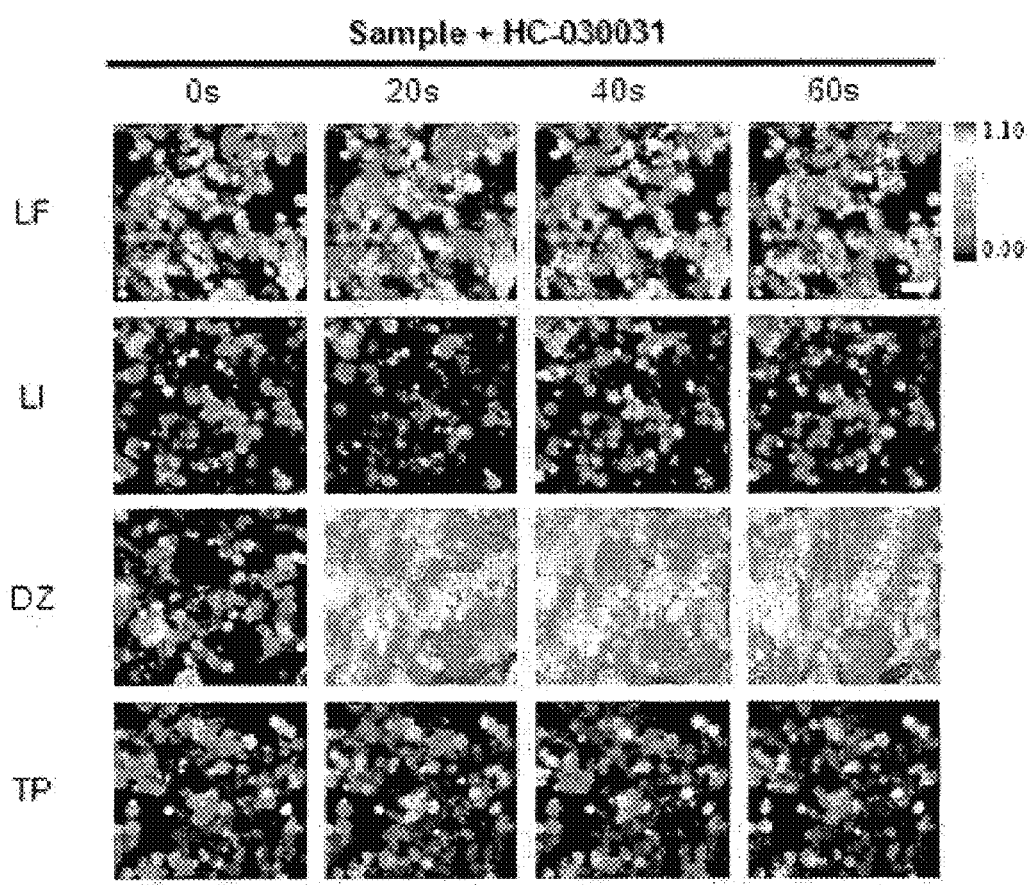
Figure 4:
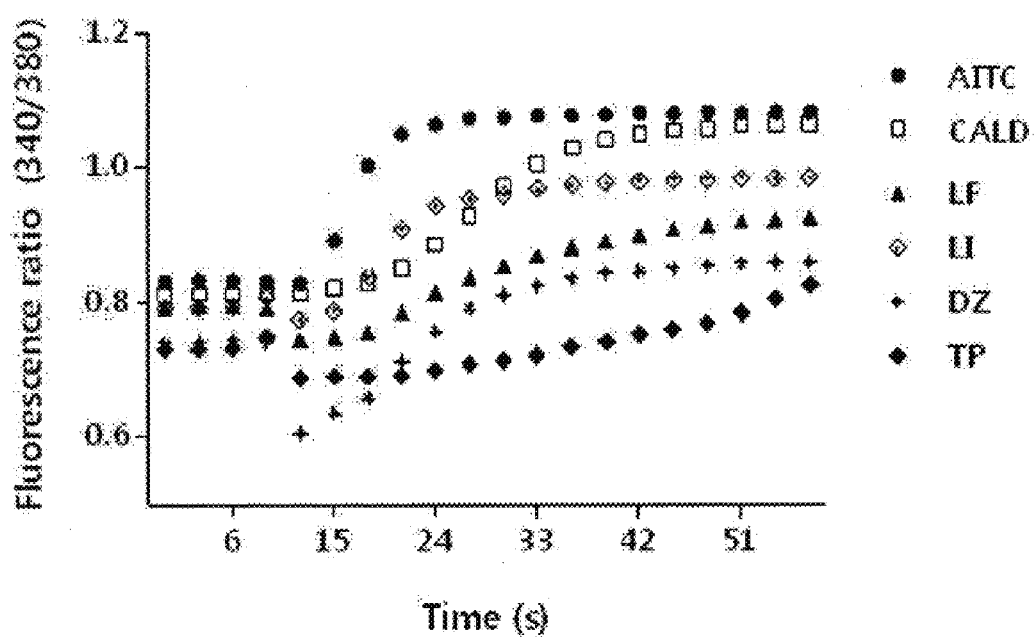
FIG. 4 illustrates results of measuring the response of hTRPA1 channel-expressing cells to extracts of the Compositae family plants using cell-based analysis. AITC (allyl isothiocyanate) and CALD (cinnamaldehyde) represent positive control groups of hTRPA1.
Figure 5A:
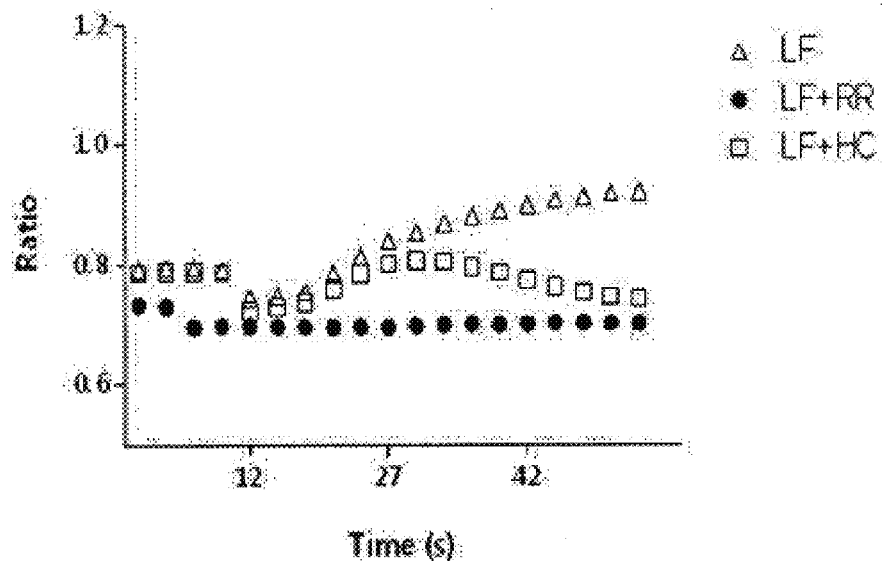
FIG. 5 illustrates results of measuring the change in $Ca^{2+}$ response when the $Ca^{2+}$ response was induced by using extracts of the Compositae family plants and then the TRP channel blocker RR or TRPA1 antagonist HC-030031 was added.
Figure 5B:
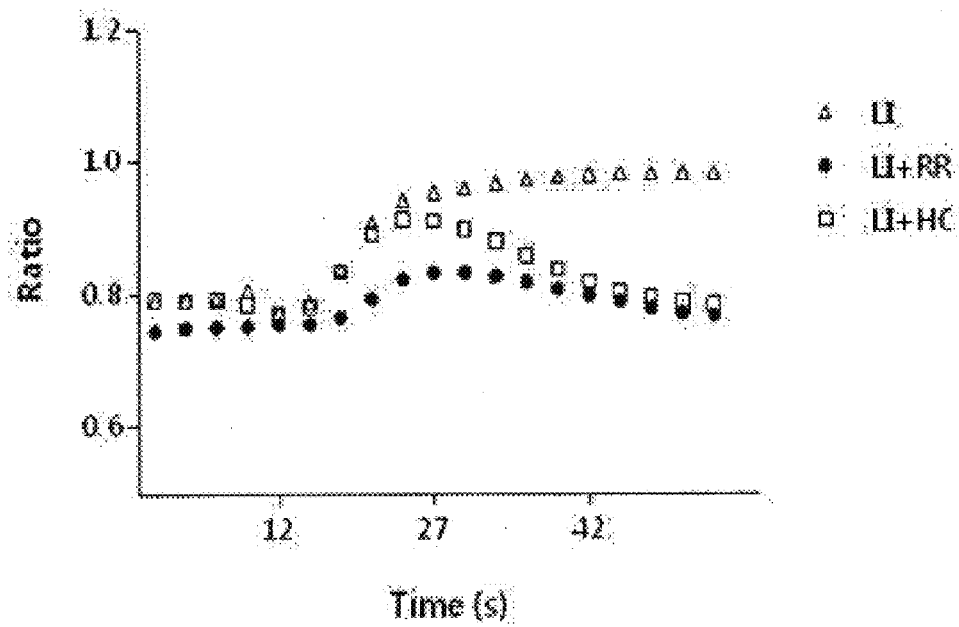
Figure 5C:
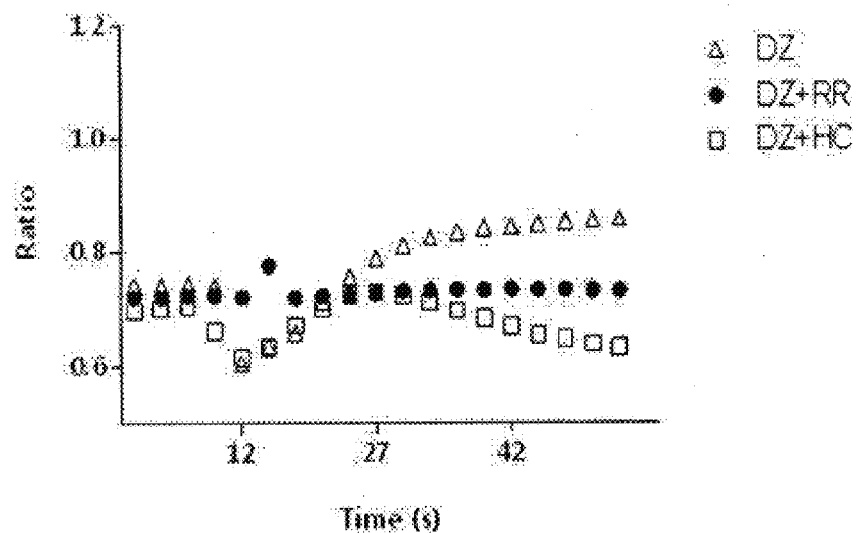
Figure 5D:
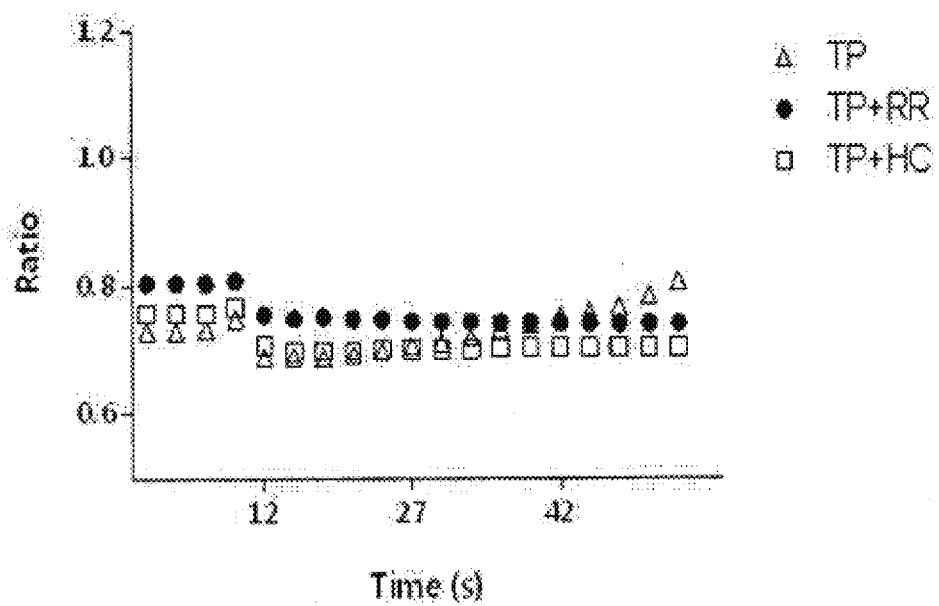

The intensity of calcium response when hTRPA1-expressed cells were treated with extracts of 4 species of the Compositae family plants was shown based on the responded cells in FIG. 3. It was confirmed that all cells were activated for the treatment with each of allyl isothiocyanate (AITC) and cinnamaldehyde (CALD) known as hTRPA1 agonists, but most activities were inhibited for the treatment with the cationic channel blocker ruthenium red (RR), and AITC activity was not inhibited for the treatment with HC-030031 as a TRPA1 antagonist. The reason is determined to be that AITC passes through the TRPV1 channel as well as the TRPA1 channel. For the four selected plants, all samples were confirmed to show 80% or higher activity. Of these, the activity inhibition by HC-030031 was not completely achieved in LI, and thus, LI is determined to pass through another channel besides the TRPA1 channel.

In Korea, LF (*Ligularia fischeri* (Ledeb.) Turcz.), LI (*Lactuca indica* L.), and TP (*Taraxacum platycarpum* Dahlst.) have been used mainly as plant food materials, that is, wild greens, and DZ (*Dendranthema zawadskii* var. *latilobum* (Maxim.) Kitam.) is a medicinal plant and thus has been used as a medicinal material in the traditional remedies. Of these, LF and LI are considered to be highly useful as foods, rather than the treatment for the purpose of special pharmacological actions exhibited in the human body The above-mentioned plants ingested for improvement of flavor or appetite in a general diet are determined to contain TRPA1 stimulating and activating materials that have previously been known or new ingredients that have never been reported. Therefore, Korean wild greens that have long been used for food have TRPA1 regulating activity, and thus can be expected to exhibit useful activity on the human body.

6. Extracts of Labiatae Family Plants

Figure 6A:
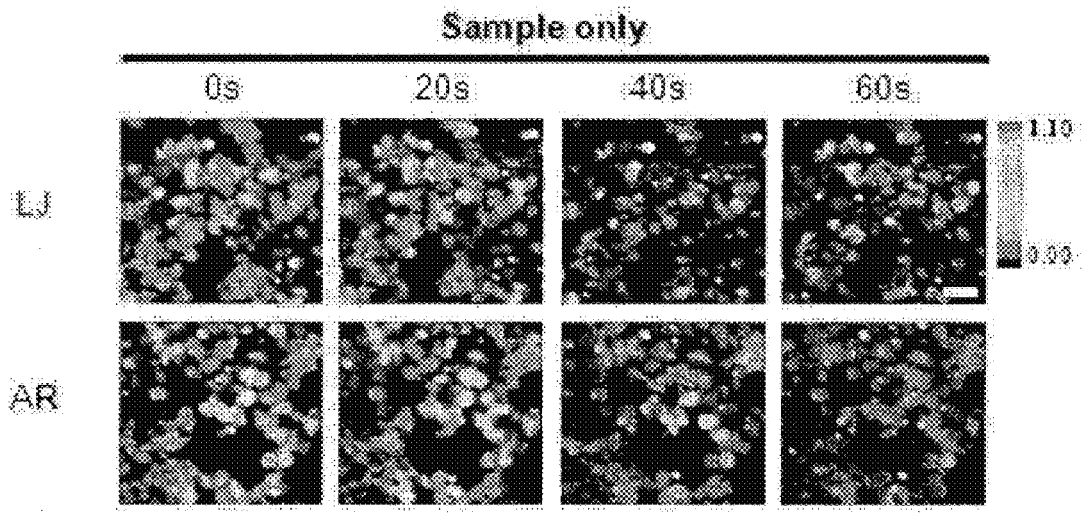
FIG. 6 illustrates images showing the response of hTRPA1 channel-expressing cells to extracts of 2 species of the family Labiatae through $Ca^{2+}$ imaging analysis. RR represents the treatment with the TRP channel blocker, ruthenium red (RR), and HC-030031 represents the treatment with TRPA1-specific antagonist HC-030031.
Figure 6B:
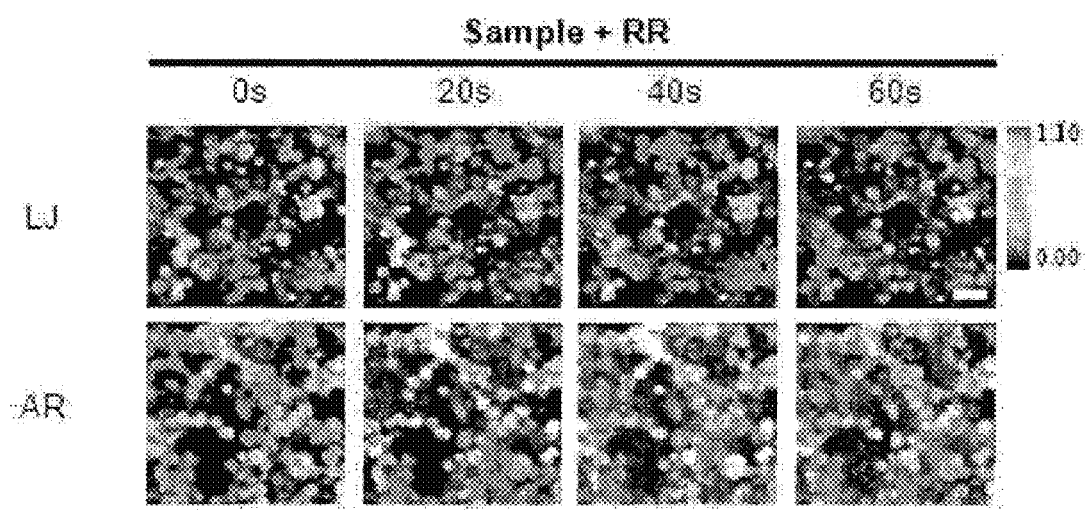
Figure 6C:
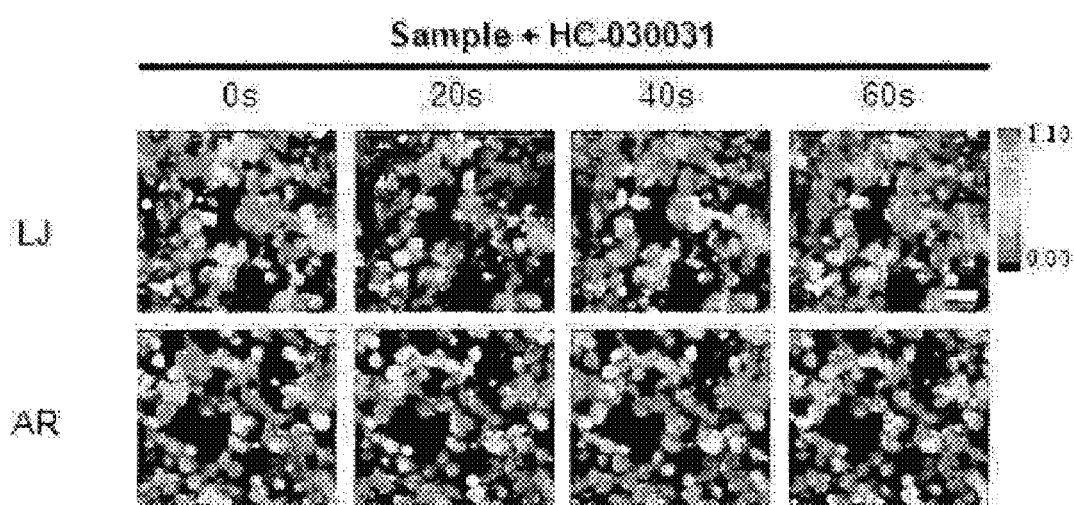

The intensity of calcium response when hTRPA1-expressed cells were treated with extracts of 2 species of the Compositae family plants was shown based on the responded cells in FIG. 6. It was confirmed that all cells were activated for the treatment with each of allyl isothiocyanate (AITC) and cinnamaldehyde (CALD) known as hTRPA1 agonists, but most activities were inhibited for the treatment with the cationic channel blocker ruthenium red (RR), and AITC activity was not inhibited for the treatment with HC-030031 as a TRPA1 antagonist. The reason is determined to be that AITC passes through TRPV1 channel as well as TRPA1 channel. For the two selected plants, LJ (*Leonurus japonicus* Houtt.) and AR (*Agastache rugosa* (Fisch. & Mey.) Kuntze) samples were confirmed to show 900 or higher activity. However, as for LJ, the activity inhibition by RR and HC-030031 was not achieved at the initial time, but mostly achieved at 60 seconds. This suggests that isothiocyanate as a main ingredient of *Leonurus japonicus* Houtt. has a remarkably high concentration or may pass through another channel other than TRPA1. In addition, the activity inhibition by HC-030031 was not completely achieved in AR, which suggests that AR may pass through another channel besides TRPA1.

Figure 7:
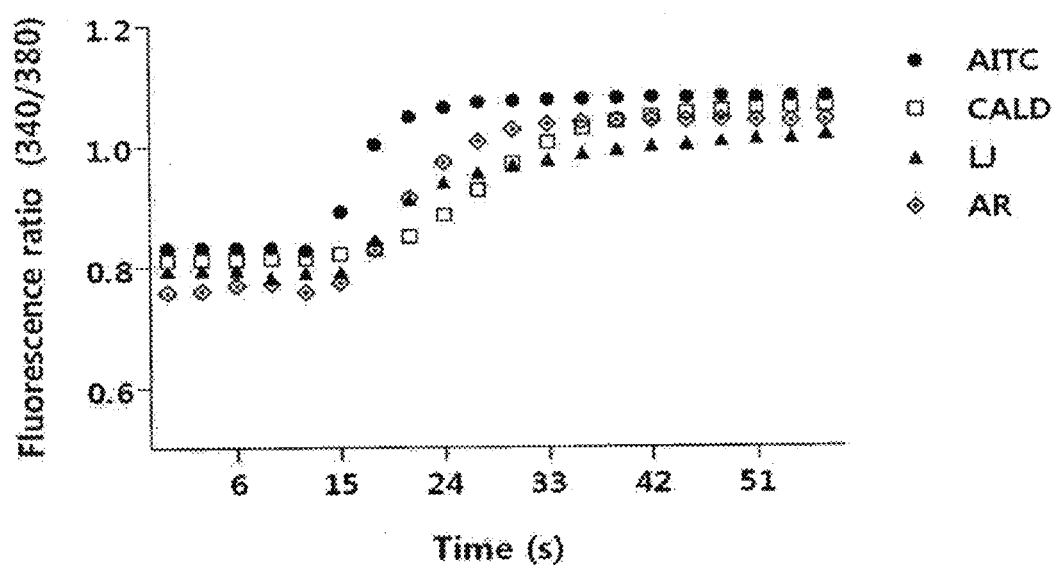
FIG. 7 illustrates results of measuring the response of hTRPA1 channel-expressing cells to extracts of the Labiatae family plants using cell-based analysis. AITC (allyl isothiocyanate) and CALD (cinnamaldehyde) represent positive control groups of hTRPA1.
Figure 8A:
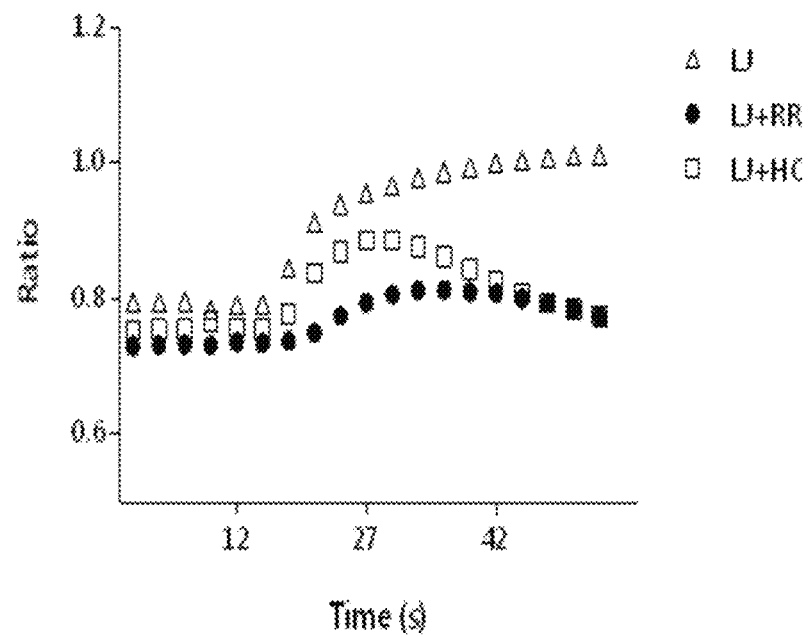
FIG. 8 illustrates results of measuring the change in $Ca^{2+}$ response when the $Ca^{2+}$ response was induced by using extracts of the Labiatae family plants and then the TRP channel blocker RR or TRPA1 antagonist HC-030031 was added.
Figure 8B:
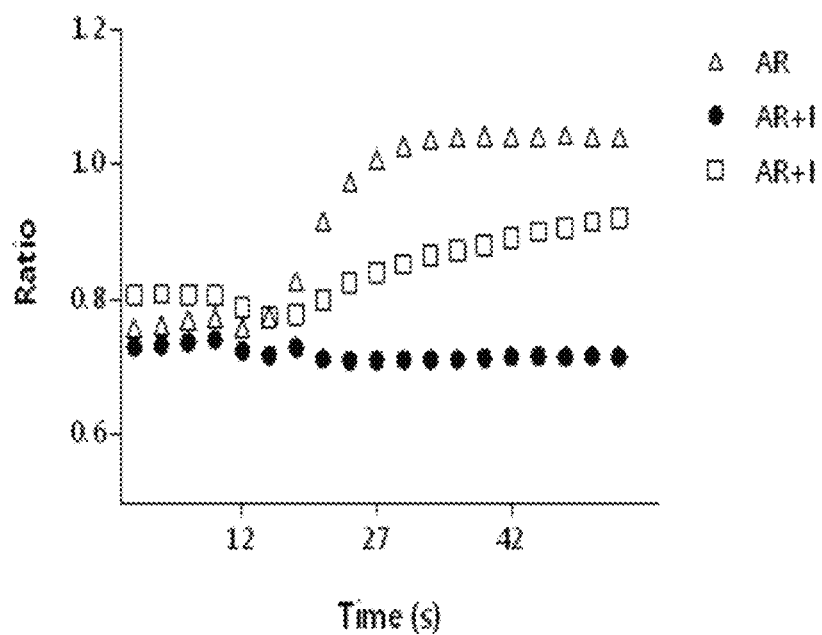

Meanwhile, LJ and AR activated hTRPA1 to a similar level as AITC and CALD which are positive control groups of hTRPA1 (FIG. 7). The $Ca^{2+}$ response induced by LJ or AR was inhibited by the cationic channel blocker RR (30 μM) and TRPA1 antagonist HC-030031 (100 μM) (FIG. 8).

7. Extracts of Liliaceae Family Plants

Figure 9A:
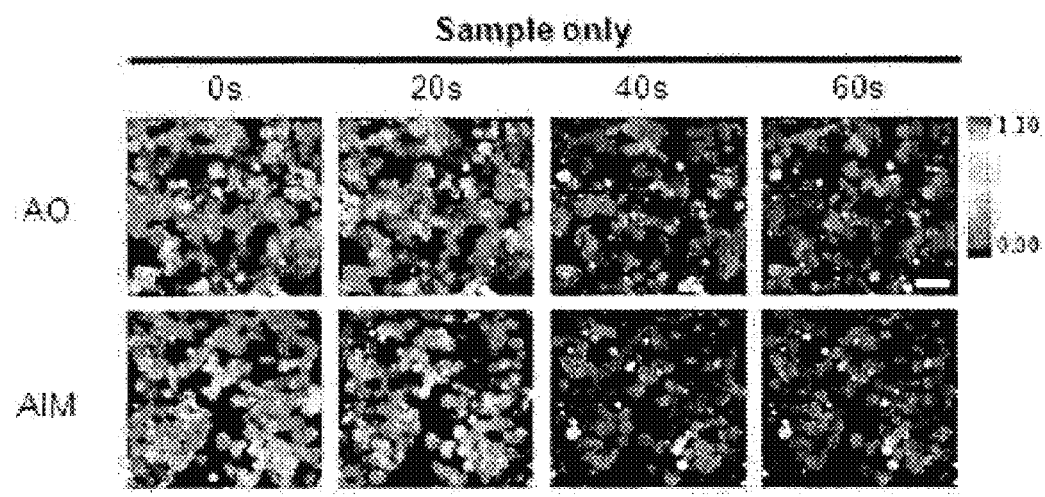
FIG. 9 illustrates images showing the response of hTRPA1 channel-expressing cells to extracts of 2 species of the family Liliaceae through $Ca^{2+}$ imaging analysis. RR represents the treatment with the TRP channel blocker, ruthenium red (RR), and HC-030031 represents the treatment with TRPA1-specific antagonist HC-030031.
Figure 9B:
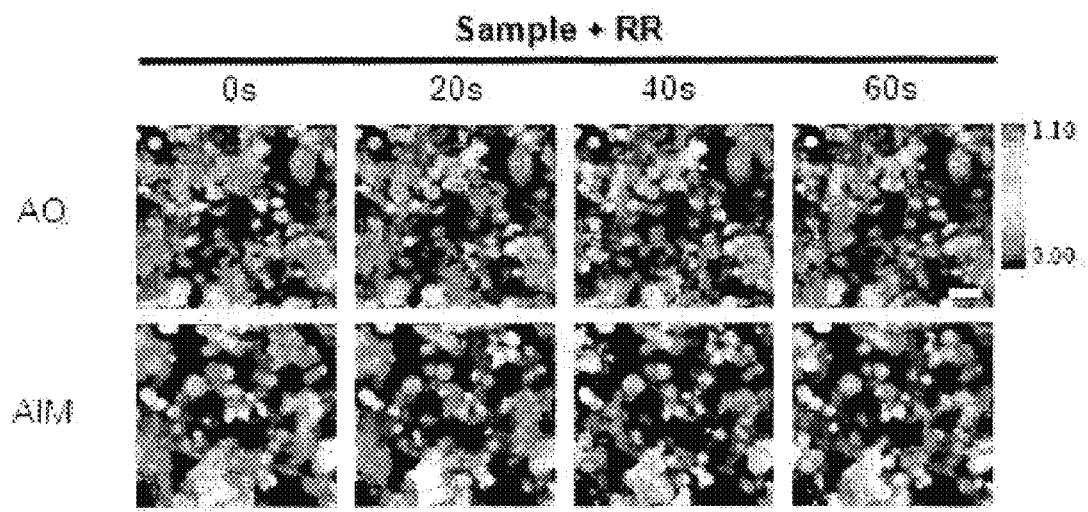
Figure 9C:
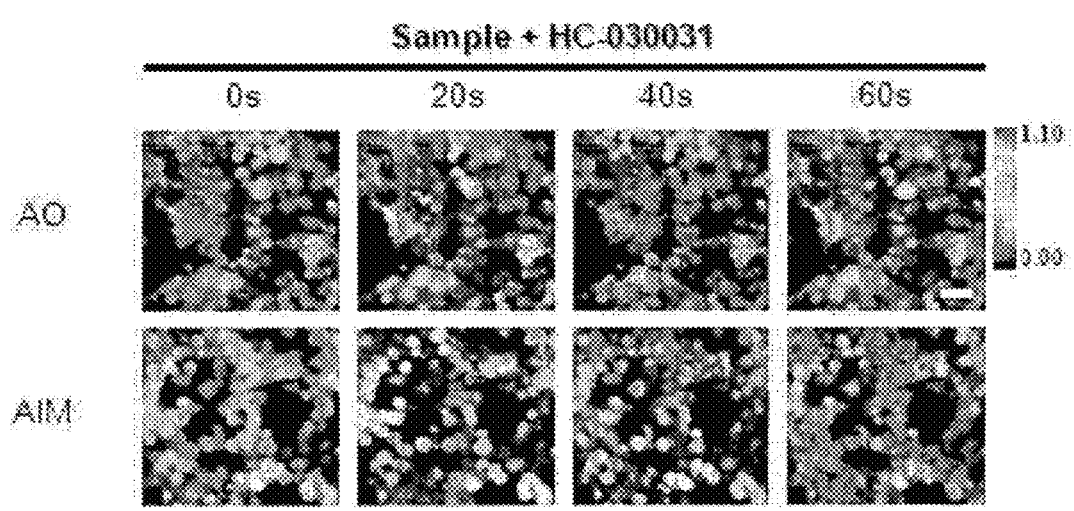

The intensity of calcium response when hTRPA1-expressed cells were treated with extracts of 2 species of the Liliaceae family plants was shown based on the responded cells in FIG. 9. It was confirmed that all cells were activated for the treatment with each of allyl isothiocyanate (AITC) and cinnamaldehyde (CALD) known as hTRPA1 agonists, but most activities were inhibited for the treatment with the cationic channel blocker ruthenium red (RR), and AITC activity was not inhibited for the treatment with HC-030031 as a TRPA1 antagonist. The reason is determined to be that AITC passes through the TRPV1 channel as well as the TRPA1 channel. For the two selected plants, AO (*Allium ochotense* Prokh.) and AlM (*Allium monanthum* Maxim.) samples were confirmed to show 900 or higher activity. However, as for AO, the activity inhibition by HC-030031 was not partially achieved at the initial time, but was completely achieved at 60 seconds. This suggests that isothiocyanate as a main ingredient of the leaf of *Wasabia japonica* (Miq.) Matsum. has a remarkably high concentration or may pass through another channel other than TRPA1. In addition, the activity inhibition by RR and HC-030031 was not completely achieved in AlM, which suggests that AIM may pass through another channel besides TRPA1.

Figure 10:
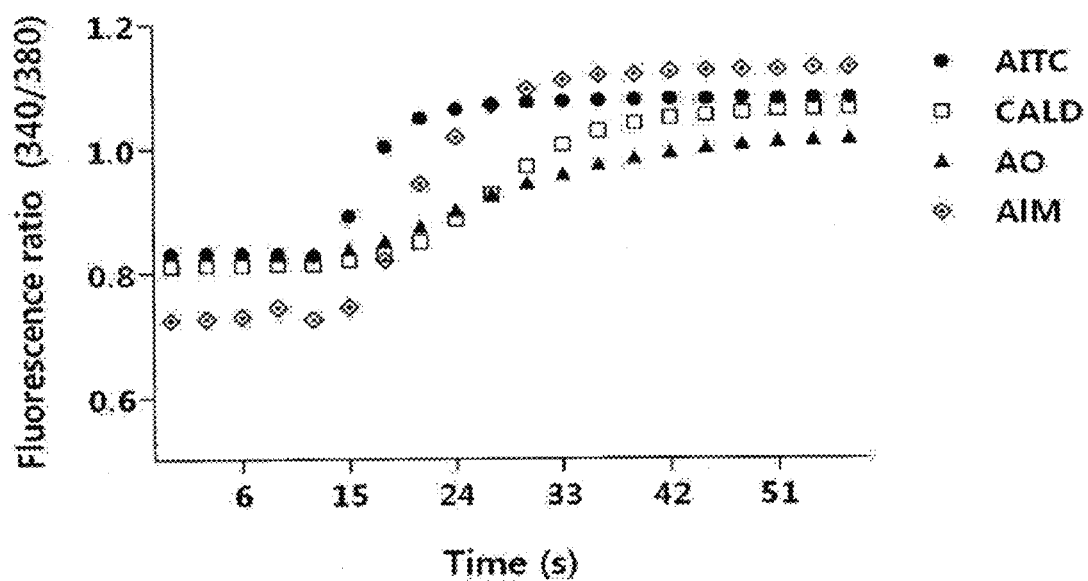
FIG. 10 illustrates results of measuring the response of hTRPA1 channel-expressing cells to extracts of the Liliaceae family plants using cell-based analysis. AITC (allyl isothiocyanate) and CALD (cinnamaldehyde) represent positive control groups of hTRPA1.
Figure 11A:
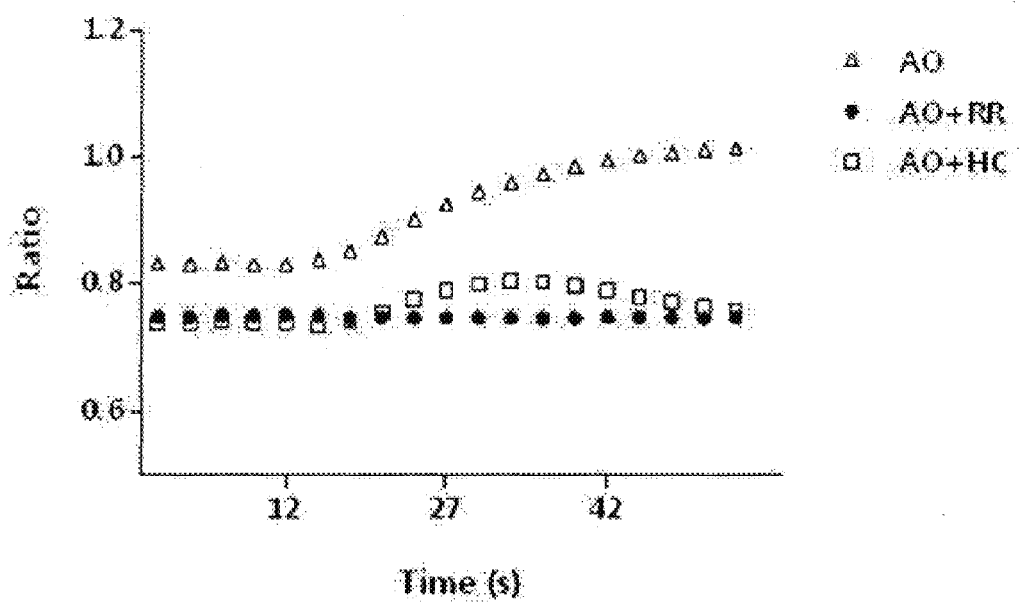
FIG. 11 illustrates results of measuring the change in $Ca^{2+}$ response when the $Ca^{2+}$ response was induced by using extracts of the Liliaceae family plants and then the TRP channel blocker RR or TRPA1 antagonist HC-030031 was added.
Figure 11B:
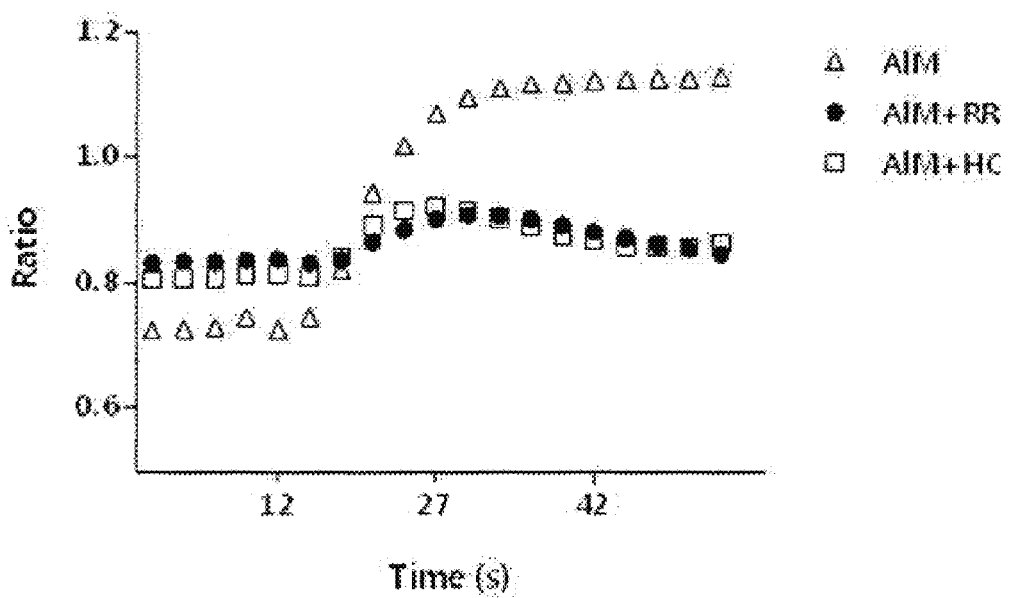

Meanwhile, AO and AIM activated hTRPA1 to a similar level as AITC and CALD which are positive control groups of hTRPA1 (FIG. 10). The $Ca^{2+}$ response induced by AO or AIM was inhibited by the cationic channel blocker RR (30 μM) and TRPA1 antagonist HC-030031 (100 μM) (FIG. 11).

8. Extract of Amaranthaceae Family Plant

Figure 12A:
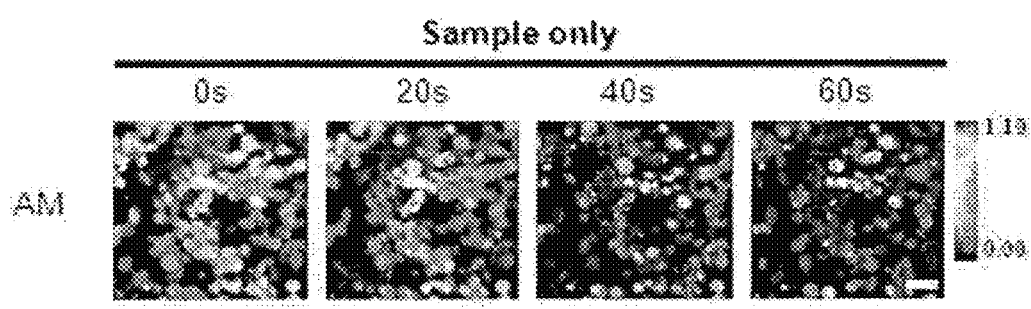
FIG. 12 illustrates images showing the response of hTRPA1 channel-expressing cells to extracts of 1 species of the family Amaranthaceae through $Ca^{2+}$ imaging analysis. RR represents the treatment with the TRP channel blocker, ruthenium red (RR), and HC-030031 represents the treatment with TRPA1-specific antagonist HC-030031.
Figure 12B:
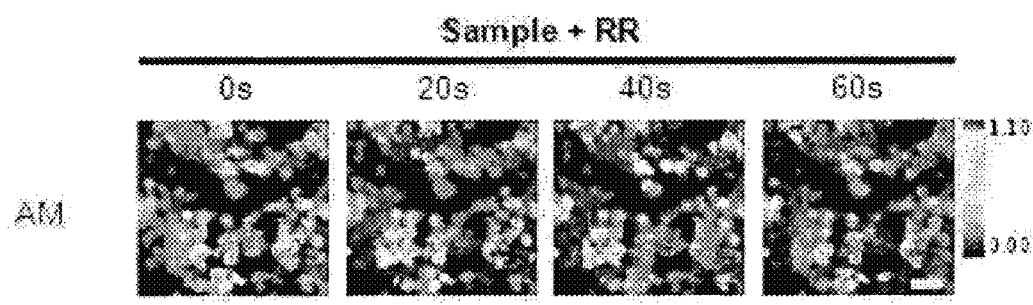
Figure 12C:
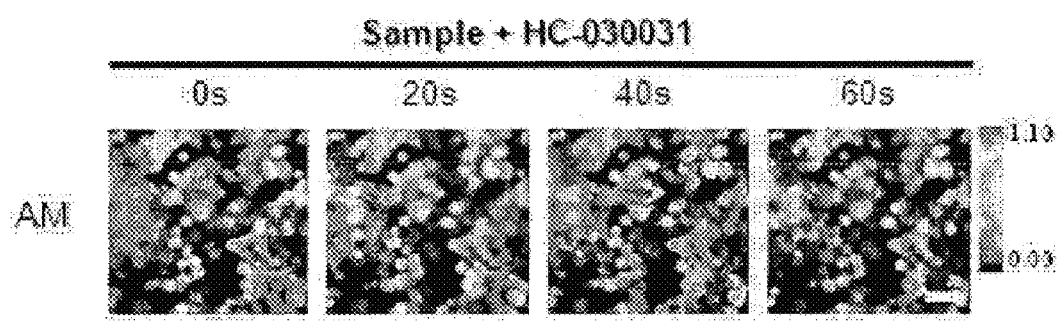

The intensity of calcium response when hTRPA1-expressed cells were treated with an extract of 1 species of the Amaranthaceae family plants was shown based on the responded cells in FIG. 12. It was confirmed that all cells were activated for the treatment with each of allyl isothiocyanate (AITC) and cinnamaldehyde (CALD) known as hTRPA1 agonists, but most activities were inhibited for the treatment with the general blocker of the cationic channel, ruthenium red (RR), and AITC activity was not inhibited for the treatment with HC-030031 as a TRPA1 antagonist. The reason is determined to be that AITC passes through the TRPV1 channel as well as the TRPA1 channel. The selected *Amaranthus mangostanus* L. was confirmed to show 800 or higher activity as compared with the positive control groups AITC and CALD. However, the activity inhibition by HC-030031 was not partially achieved at the initial time, but was completely achieved at 60 seconds.

Figure 13:
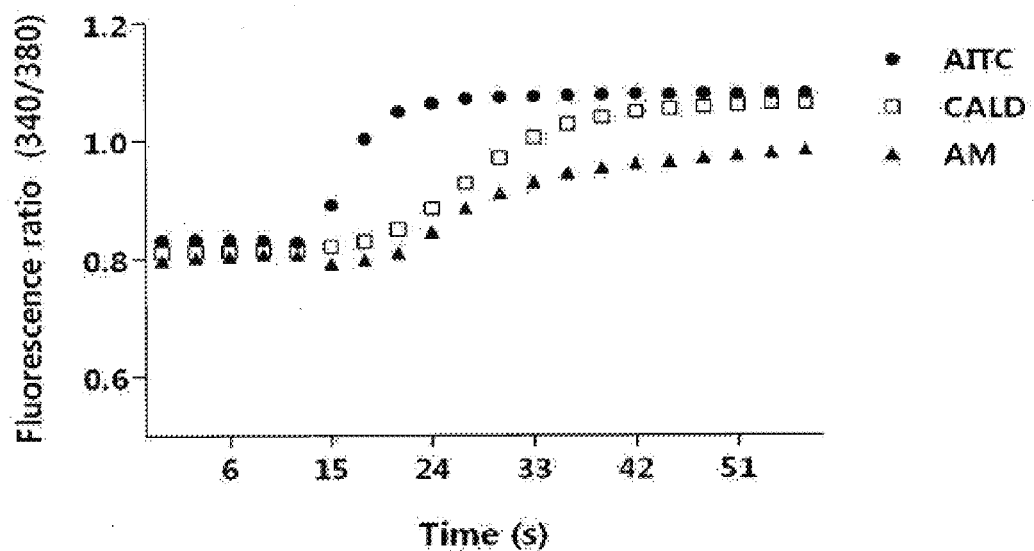
FIG. 13 illustrates results of measuring the response of hTRPA1 channel-expressing cells to extracts of the Amaranthaceae family plants using cell-based analysis. AITC (allyl isothiocyanate) and CALD (cinnamaldehyde) represent positive control groups of hTRPA1.
Figure 14:
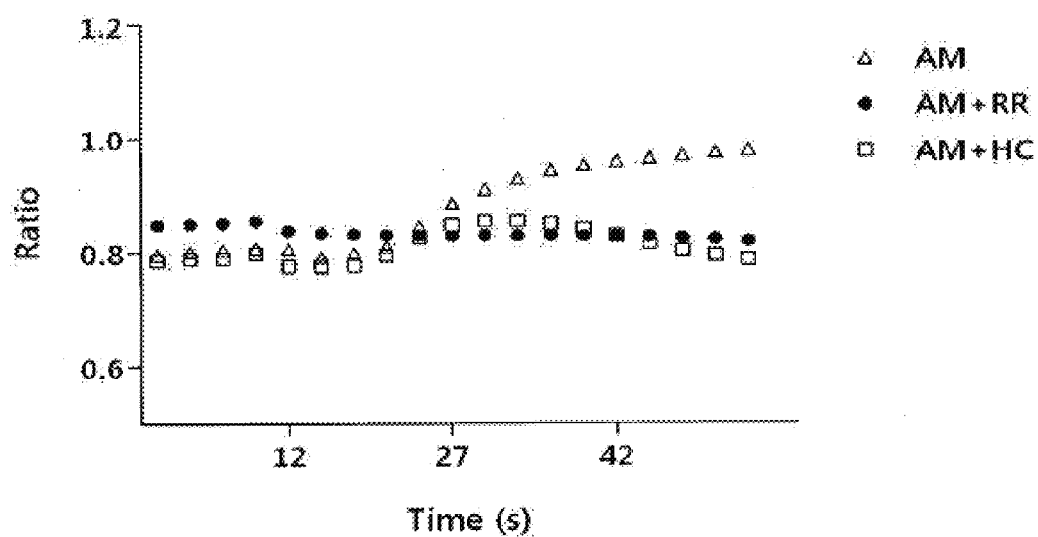
FIG. 14 illustrates results of measuring the change in $Ca^{2+}$ response when the $Ca^{2+}$ response was induced by using extracts of the Amaranthaceae family plants and then the TRP channel blocker RR or TRPA1 antagonist HC-030031 was added.

Meanwhile, AM (*Amaranthus mangostanus* L.) activated hTRPA1 to a similar level as AITC and CALD which are positive control groups of hTRPA1 (FIG. 13). The $Ca^{2+}$ response induced by AM was inhibited by the cationic channel blocker RR (30 μM) and TRPA1 antagonist HC-030031 (100 μM) (FIG. 14).

In Korea, LJ and AR have been mainly used as a medicinal plant or an herbal plant, and AO, AlM, and AM have been mainly used as food materials, that is, wild greens. The above plants are considered to be highly useful as foods, rather than the treatment for the purpose of special pharmacological actions exhibited in the human body The above-mentioned plants which are ingested for improvement of flavor or appetite in a general diet are determined to contain TRPA1 stimulating and activating materials or new ingredients that have never been reported. Therefore, Korean wild greens that have long been used for food have TRPA1 regulating activity, and thus can be expected to exhibit useful activity on the human body.

9. Extracts of Brassicaceae Family Plants

Figure 15A:
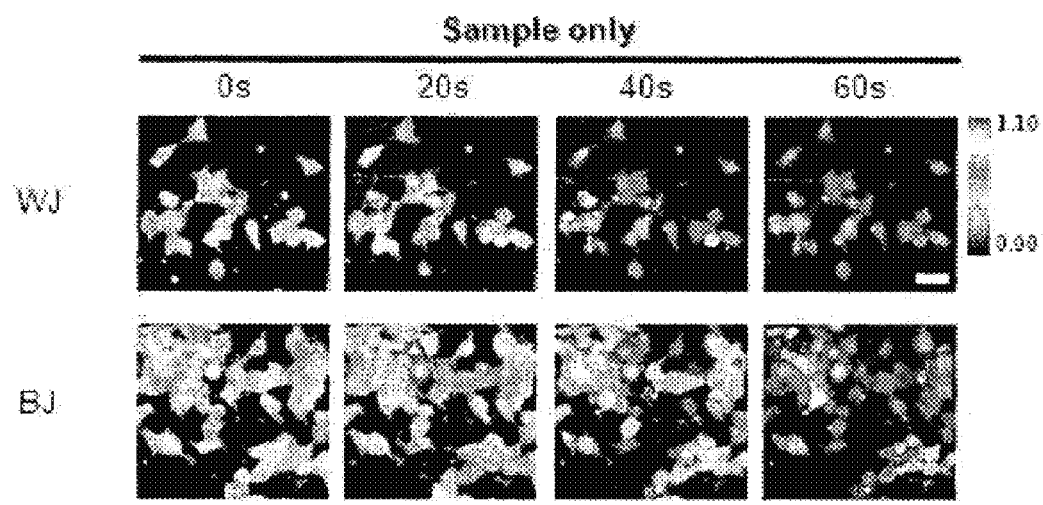
FIG. 15 illustrates images showing the response of hTRPA1 channel-expressing cells to extracts of 2 species of the family Brassicaceae through $Ca^{2+}$ imaging analysis. RR represents the treatment with the TRP channel blocker, ruthenium red (RR), and HC-030031 represents the treatment with TRPA1-specific antagonist HC-030031.
Figure 15B:
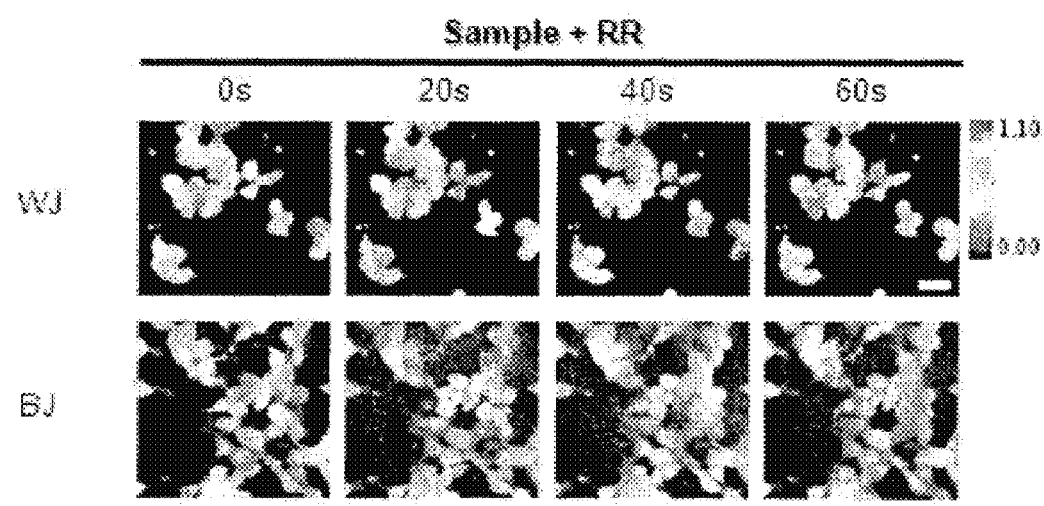
Figure 15C:
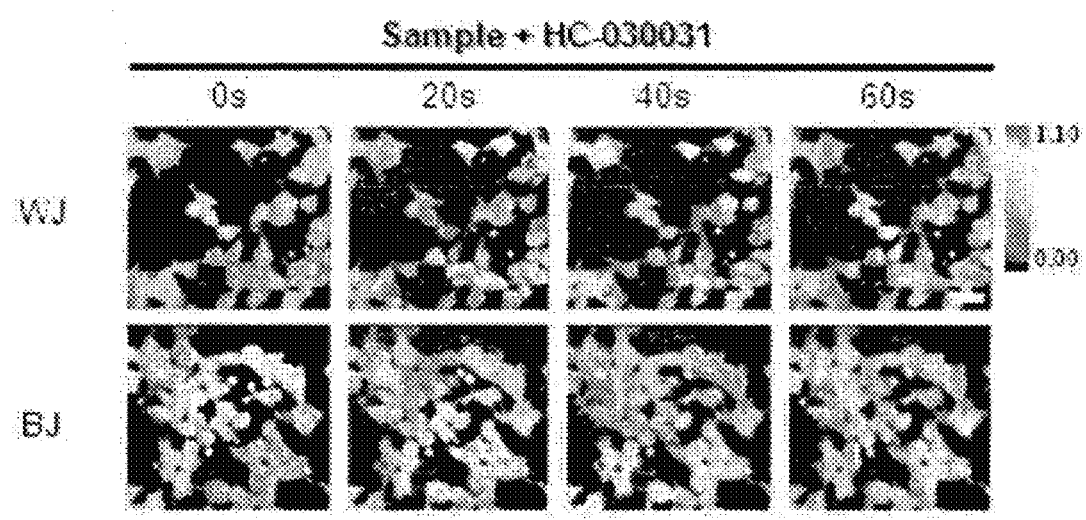

The intensity of calcium response when hTRPA1-expressed cells were treated with extracts of 2 species of the Brassicaceae family plants were shown based on the responded cells in FIG. 15. It was confirmed that all cells were activated for the treatment with each of allyl isothiocyanate (AITC) and cinnamaldehyde (CALD) known as hTRPA1 agonists, but most activities were inhibited for the treatment with the cationic channel blocker ruthenium red (RR), and AITC activity was not inhibited for the treatment with HC-030031 as a TRPA1 antagonist. The reason is determined to be that AITC passes through the TRPV1 channel as well as the TRPA1 channel. For the two selected plants, WJ and BJ samples were confirmed to show 900 or higher activity. However, as for WJ, the activity inhibition by RR and HC-030031 was not achieved at the initial time, but was completely achieved at 60 seconds. This suggests that isothiocyanate as a main ingredient of *Wasabia japonica* (Miq.) Matsum. has a remarkably high concentration or may pass through another channel other than TRPA1.

Figure 16:
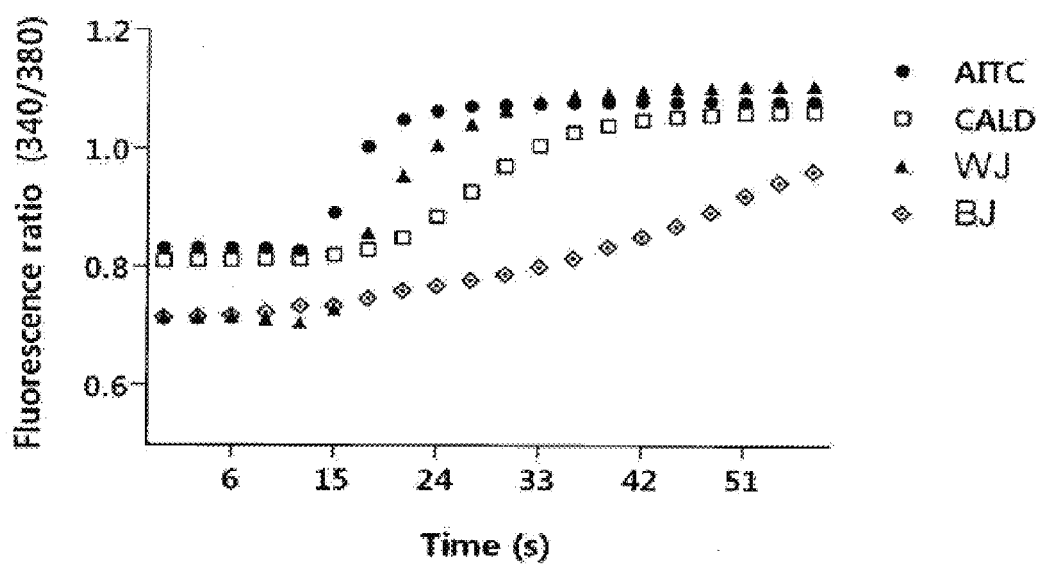
FIG. 16 illustrates results of measuring the response of hTRPA1 channel-expressing cells to extracts of the Brassicaceae family plants using cell-based analysis. AITC (allyl isothiocyanate) and CALD (cinnamaldehyde) represent positive control groups of hTRPA1.
Figure 17A:
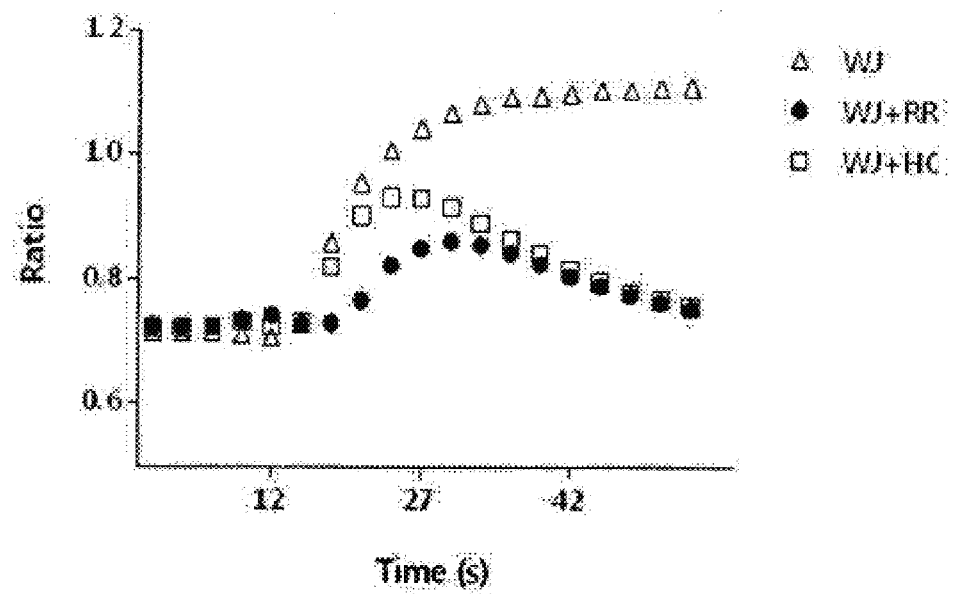
FIG. 17 illustrates results of measuring the change in $Ca^{2+}$ response when the $Ca^{2+}$ response was induced by using extracts of the Brassicaceae family plants and then the TRP channel blocker RR or TRPA1 antagonist HC-030031 was added.
Figure 17B:
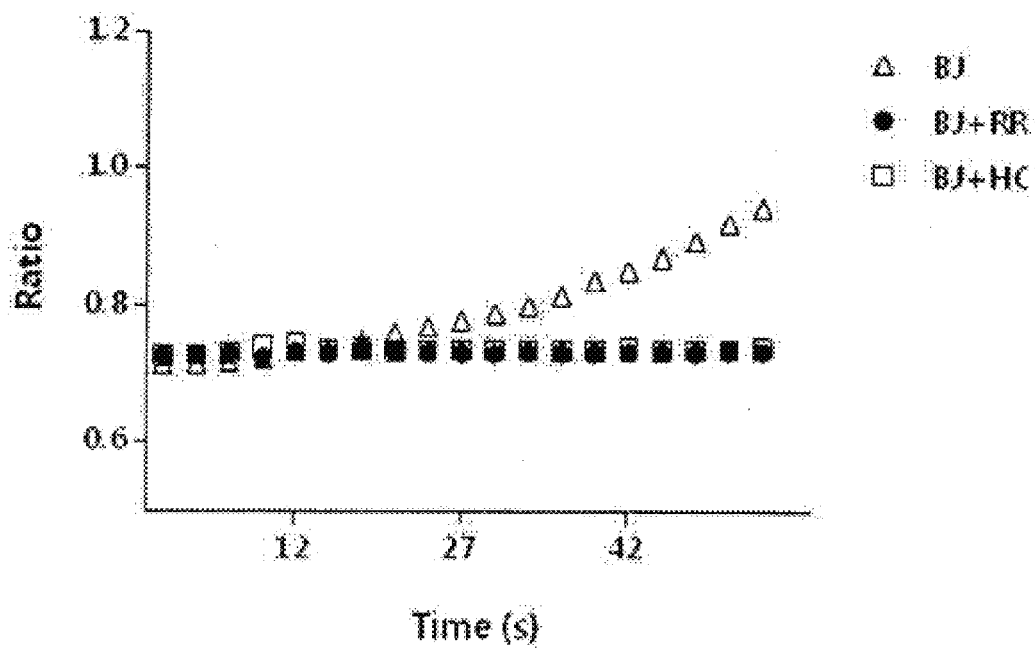

Meanwhile, WJ and BJ activated hTRPA1 to a similar level as AITC and CALD which are positive control groups of hTRPA1 (FIG. 16). The $Ca^{2+}$ response induced by WJ or BJ was inhibited by the cationic channel blocker RR (30 µM) and TRPA1 antagonist HC-030031 (100 µM) (FIG. 17).

10. Extracts of Umbelliferae Family Plants

Figure 18A:
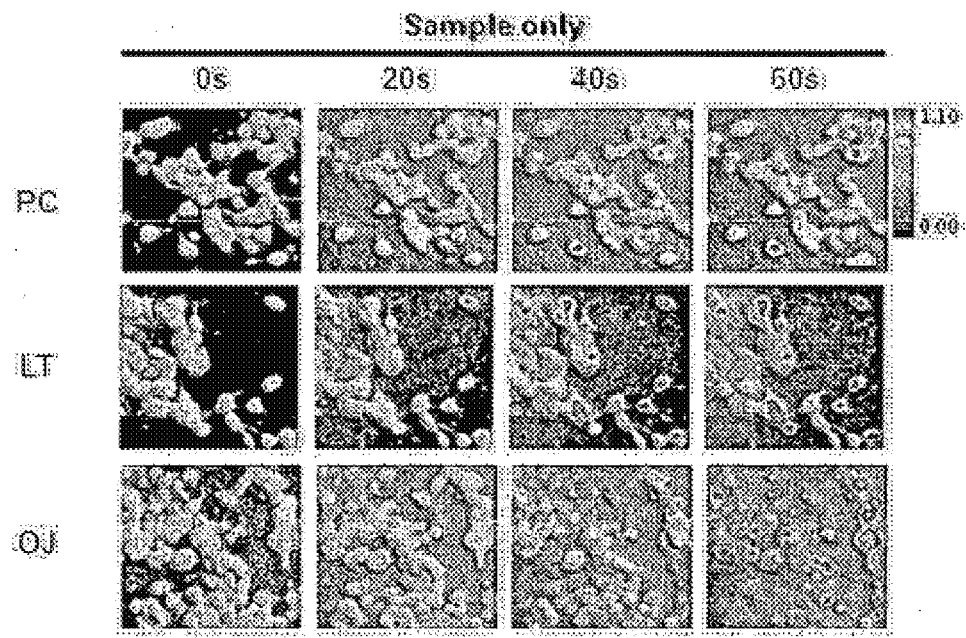
FIG. 18 illustrates images showing the response of hTRPA1 channel-expressing cells to extracts of 3 species of the family Umbelliferae through $Ca^{2+}$ imaging analysis. RR represents the treatment with the TRP channel blocker, ruthenium red (RR), and HC-030031 represents the treatment with TRPA1-specific antagonist HC-030031.
Figure 18B:
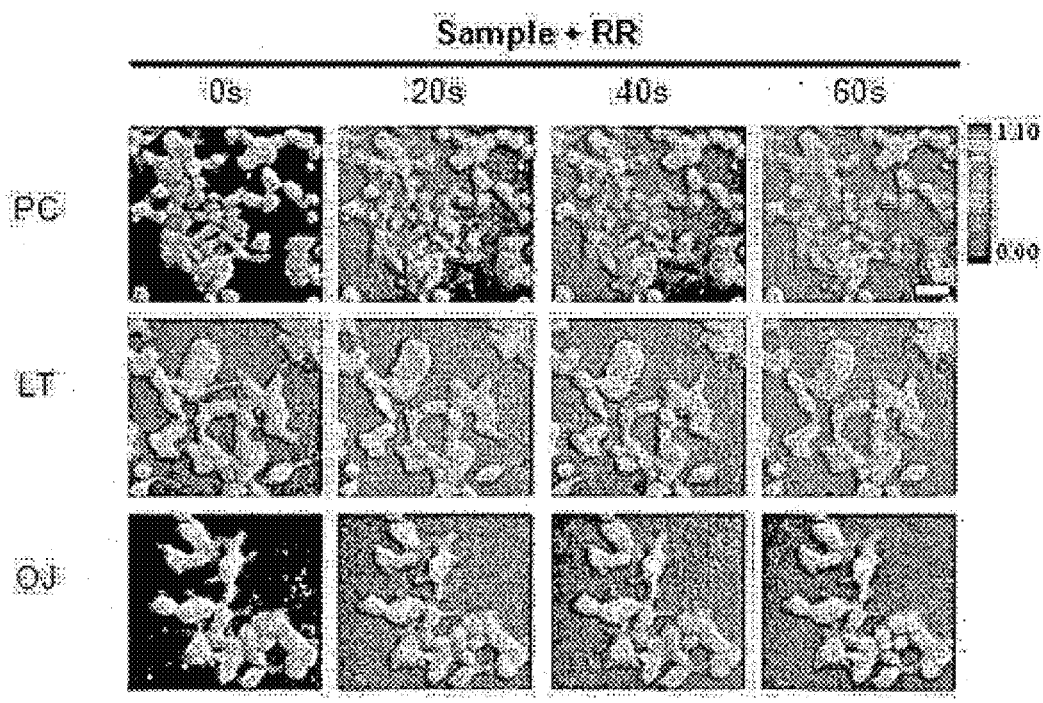
Figure 18C:
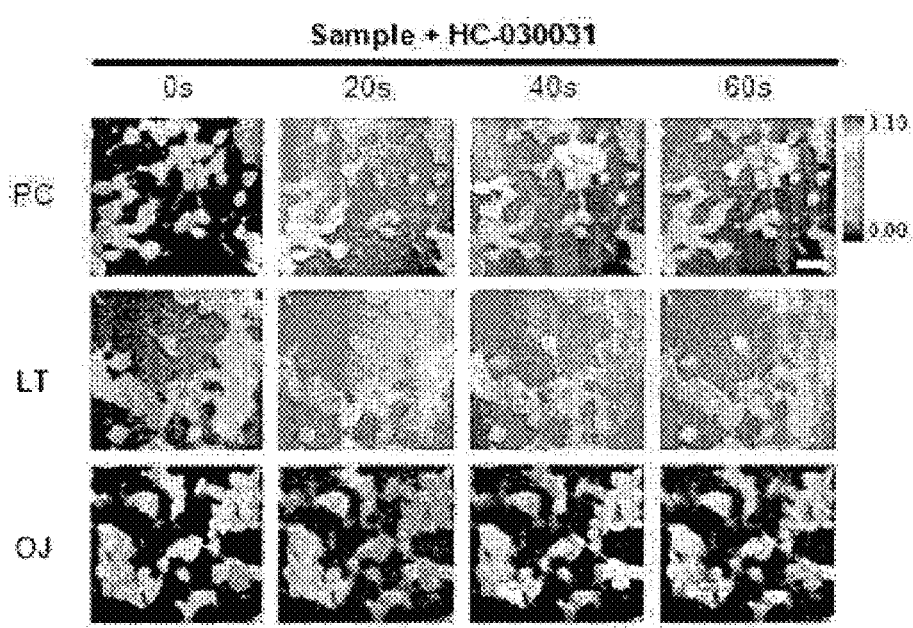
Figure 19:
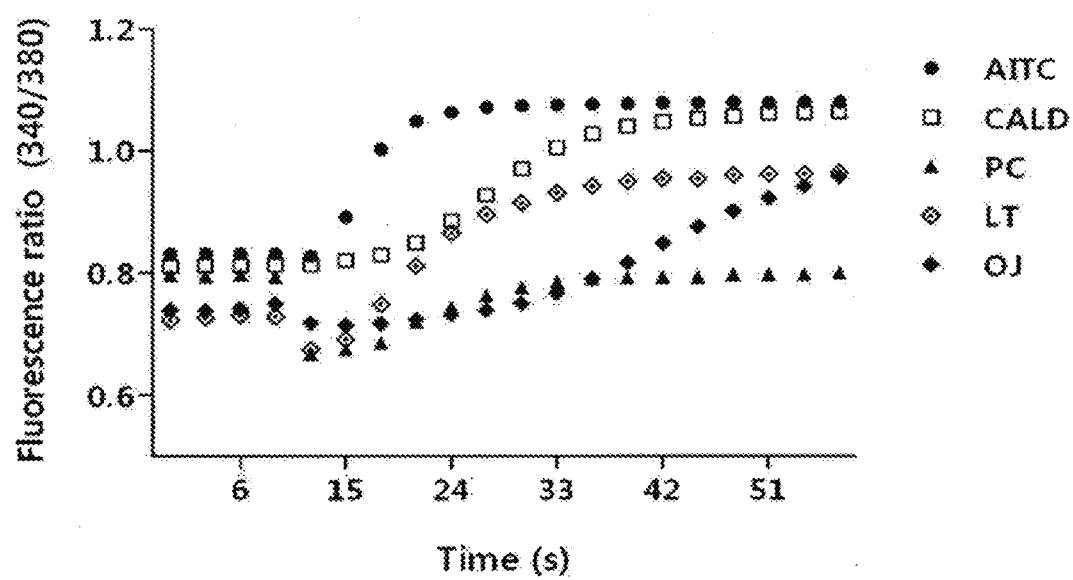
FIG. 19 shows results of measuring the response of hTRPA1 channel-expressing cells to extracts of the Umbelliferae family plants using cell-based analysis. AITC (allyl isothiocyanate) and CALD (cinnamaldehyde) represent positive control groups of hTRPA1.
Figure 20A:
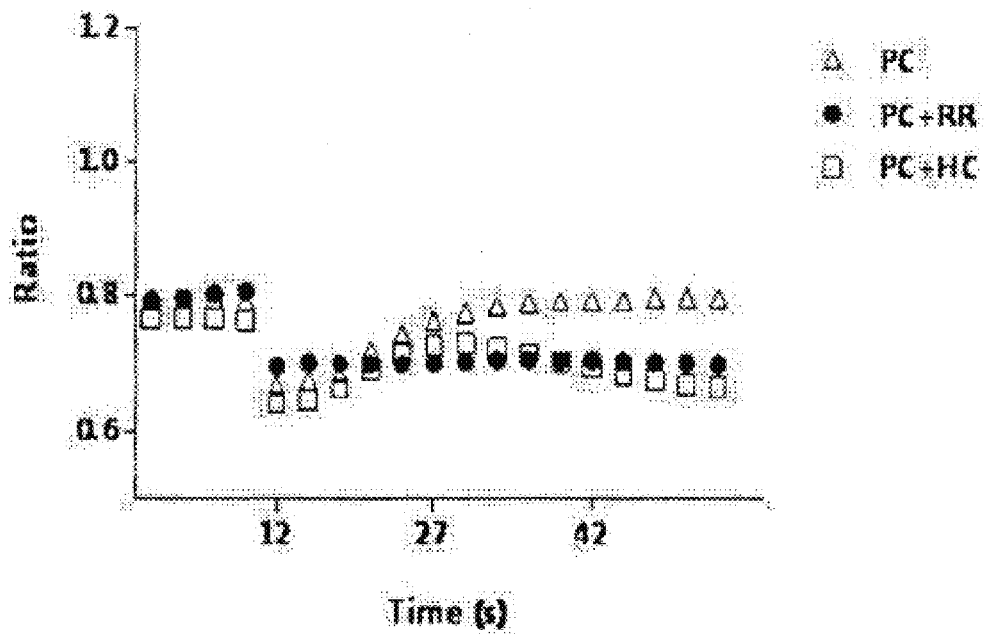
FIG. 20 illustrates results of measuring the change in $Ca^{2+}$ response when the $Ca^{2+}$ response was induced by using extracts of the Umbelliferae family plants and then the TRP channel blocker RR or TRPA1 antagonist HC-030031 was added.
Figure 20B:
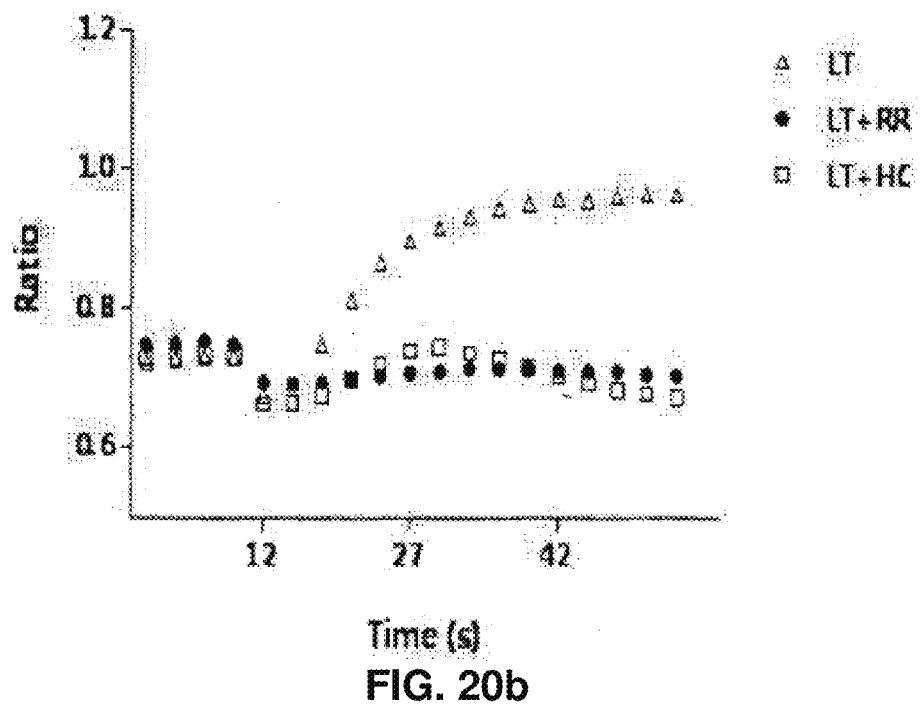
Figure 20C:
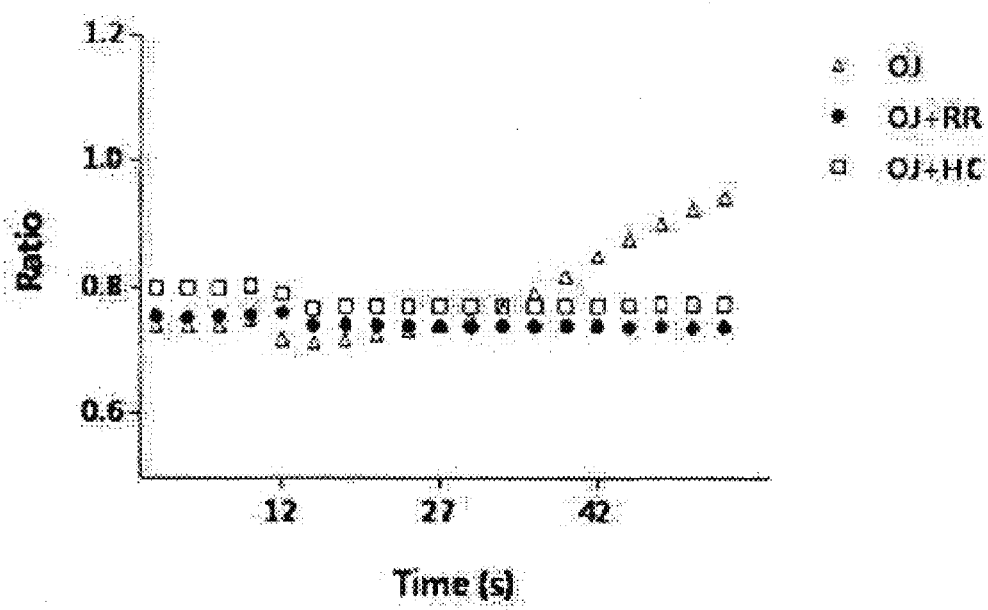

The intensity of calcium response when hTRPA1-expressed cells were treated with extracts of 3 species of the Umbelliferae family plants was shown based on the responded cells in FIG. 18. It was confirmed that all cells were activated for the treatment with each of allyl isothiocyanate (AITC) and cinnamaldehyde (CALD) known as hTRPA1 agonists, but most activities were inhibited for the treatment with the cationic channel blocker ruthenium red (RR), and AITC activity was not inhibited for the treatment with HC-030031 as a TRPA1 antagonist. The reason is determined to be that AITC passes through the TRPV1 channel as well as the TRPA1 channel. For the three selected plants, LT and OJ samples were confirmed to show 800 or higher activity, but the PC sample was confirmed to show lower activity as compared with the other two samples. The reason is that the sample is turbid due to the nature thereof, thereby recording the low value, but it is thought that this problem may be solved by using a die that cannot use the wavelength of Fura-2 but the wavelength of another region.

In Korea, WJ, BJ, PC, and OJ have been used mainly as plant food materials, that is, wild greens, and LT is a medicinal plant and thus has been used as a medicinal material in the traditional remedies. The above plants are considered to be highly useful as foods, rather than the treatment for the purpose of special pharmacological actions exhibited in the human body The above-mentioned plants ingested for improvement of flavor or appetite in a general diet are determined to contain TRPA1 stimulating and activating materials that have previously been known or new ingredients that have not been reported. Therefore, Korean wild greens that have long been used for food have TRPA1 regulating activity, and thus can be expected to exhibit useful activity on the human body.

11. HPLC Analysis of Active Ingredients of *Kalopanax pictus* Sprouts KPs Extracts It has been reported that saponine-based standard materials, such as Kalopanaxsaponin A and Kalopanaxsaponin B (hederagenin bisdesmoside), and phenolic compounds, such as syringin, methyl syringate, chlorogenic acid, coniferyl alcohol, and protocatechuic acid, are distributed in skins and leaves, but the ratio of the saponine-based compound to the phenolic compound has been known to be different for different parts. According to recent research, less saponin is contained and higher concentrations of liriodendrin and syringing are present in the skins than the leaves, and thus these two compounds are evaluated as important active materials representative to *Kalopanax*. Whereas, the *Kalopanax pictus* sprouts (*Kalopanax pictus* shoots) as wild greens for food show a high content of chlorogenic acid, and this compound is evaluated to be present as a functional compound. Based on this, as a result of ingredient analysis of six KPs fractions, chlorogenic acid was shown to have the highest content (see: FIGS. 21-26). However, the chlorogenic acid exhibited no effects in the evaluation on hTRPA1 action through $Ca^{2+}$ imaging, and it was confirmed that a small content of coniferyl alcohol confirmed as the HPLC result specifically acted on hTRPA1.

12. Evaluation of hTRPA1 Activity of *Kalopanax pictus* Sprouts KPs Fractions

Figure 27:
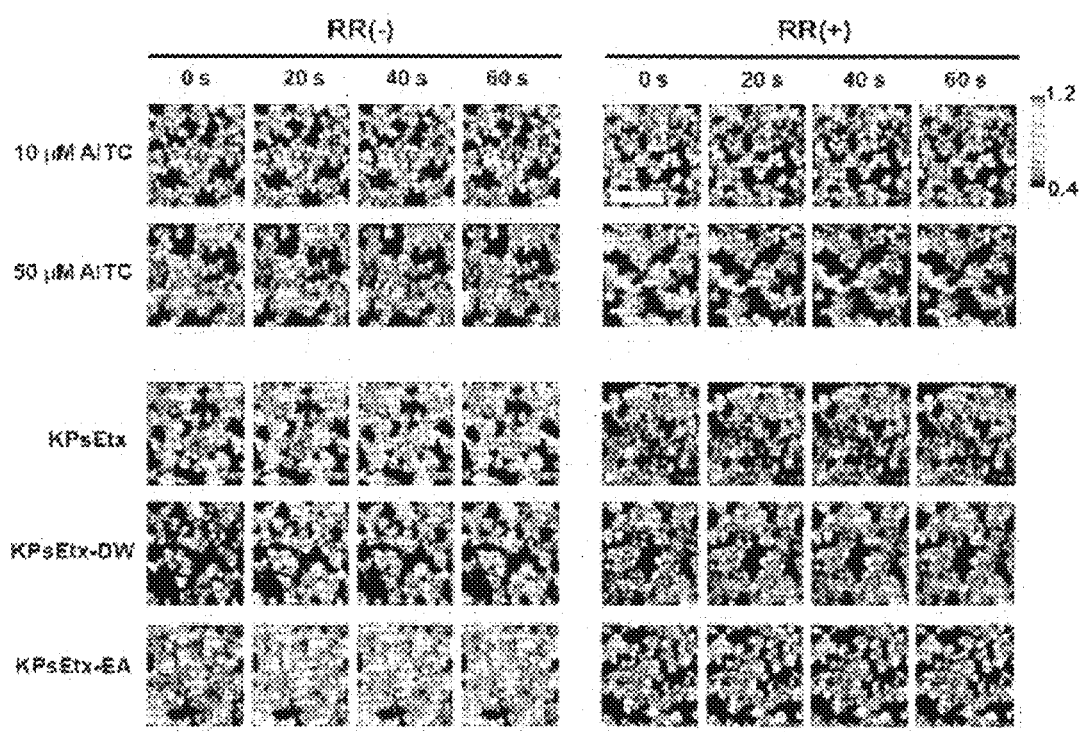
FIG. 27 illustrates images showing the response of hTRPA1 channel-expressing cells to KPs extracts through Ca2+ imaging analysis.

As for KPsEtx, KPsEtx-DW, and KPsEtx-EA, hTRPA1 activity was measured. As for KPsEtx and KPsEtx-DW, the hTRPA1 activity was inhibited in a time-dependent manner, and completely inhibited by the treatment with RR. As shown in FIG. 27, the intracellular $Ca^{2+}$ influx is considered to be shown in the same manner as compared with the treatment with allyl isothiocyanate (AITC) as a positive control group of hTRPA1, and the effects are determined to corresponding to the effects for AITC having a concentration of about 30 µM. In addition, the hTRPA1 activity was completely inhibited by RR in a time-dependent manner, and thus it is determined that the intercellular calcium concentration was further increased due to the KPs extract in the hTRPA1-stably expressing cell line (FIG. 27).

13. Evaluation of TRPA1 Activity of Coniferyl Alcohol Using $Ca^{2+}$ Imaging

Figure 28:
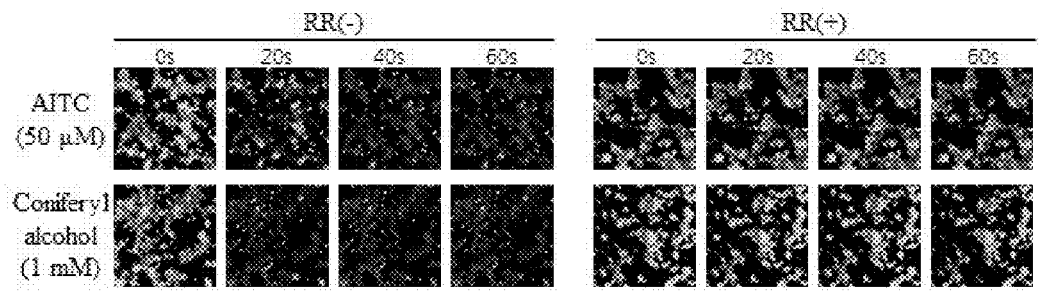
FIG. 28 illustrates images showing the response of hTRPA1 channel-expressing cells to coniferyl alcohol through Ca2+ imaging analysis. RR (−) represents the treatment with TRP channel blocker ruthenium red (RR), and RR (+) represents the non-treatment with TRP channel blocker RR. AITC (allyl isothiocyanate) was used as a positive control group.

As a result of $Ca^{2+}$ imaging in the hTRPA1-stably expressing cells, it can be seen that coniferyl alcohol increased the intercellular $Ca^{2+}$ influx in a time-dependent manner in the hTRPA1-expressed hTRPA1 stable cells, and this indicates that coniferyl alcohol activates hTRPA1 in a time-dependent manner (FIG. 28). In addition, it was confirmed that the action of coniferyl alcohol was completely blocked at the time of treatment with the general blocker of TRP channel, ruthenium red (RR, Sigma-aldrich, USA). Accordingly, it can be seen that coniferyl alcohol activates hTRPA1 to increase the intercullar $Ca^{2+}$ influx, thereby exhibiting various physiological responses by hTRPA1.

14. Evaluation of TRPA1 Activity Using Cell-Based Assay

Figure 29:
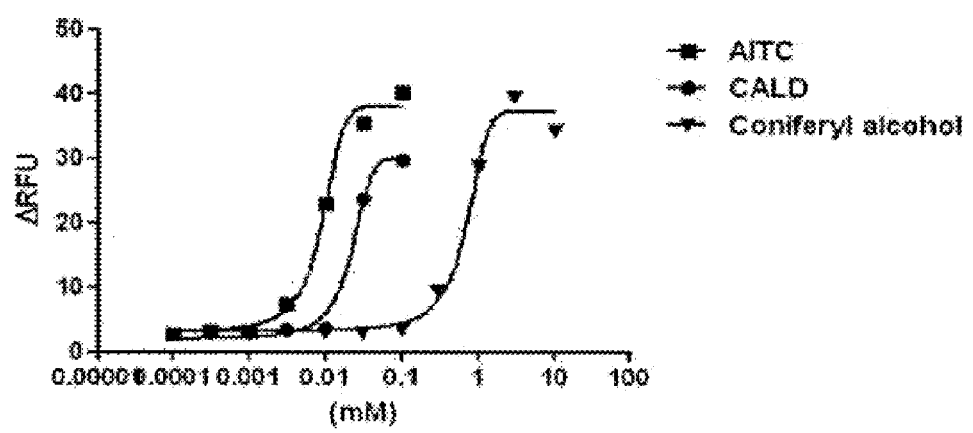
FIG. 29 shows results of measuring the response of hTRPA1 channel-expressing cells to coniferyl alcohol using cell-based analysis. AITC (allyl isothiocyanate) and (cinnamaldehyde) represent positive control groups of hTRPA1.

As the TRPA1-specific activity of coniferyl alcohol is confirmed in the foregoing experiment, the cell-based assay was used to verify the change in concentration of coniferyl alcohol and the response by HC-030031 [2-(1,3-dimethyl-2,6-dioxo-1,2,3,6-tetrahydro-7H-furin-7-yl)-N-(4-isopropylphenyl)acetamide] (Sigma-aldrich, USA), which is confirmed as a TRPA1-specific blocker. As a result of the experiment, EC50 values of coniferyl alcohol and AITC were 654.5 µM and 8.465 µM (FIG. 29). Accordingly, it can be seen that the coniferyl alcohol of the present invention is an excellent hTRPA1 agonist.

Figure 30:
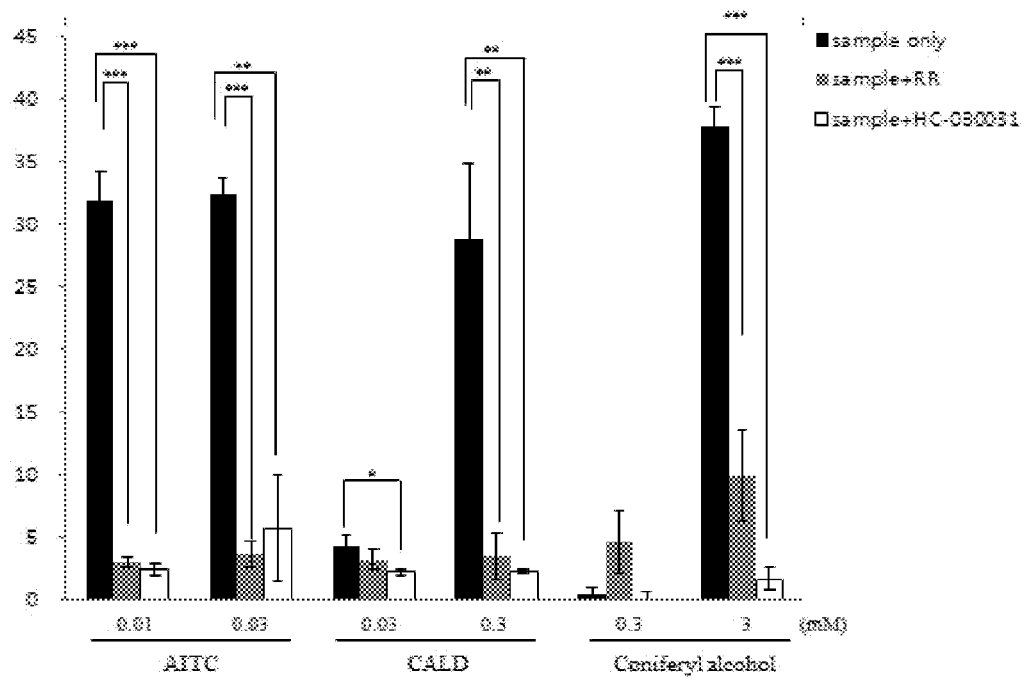
FIG. 30 is a graph showing results when the Ca2+ response was induced by using coniferyl alcohol and then the hTRPA1 antagonist HC-030031 was added. AITC (allyl isothiocyanate) and (cinnamaldehyde) represent positive control groups of hTRPA1. The $Ca^{2+}$ response induced by coniferyl alcohol was inhibited by the cationic channel blocker RR (30 µM) and TRPA1 antagonist HC-030031 (100 µM). Black columns represent TRPA1 activity by AITC (0.01, 0.03 mM), CALD (0.03, 0.3 mM), and coniferyl alcohol (0.1, 3 mM). Grey and white columns represent TRPA1 activities for the treatment with RR and HC-30031, respectively. Each column was expressed by the mean±SEM. *, , and * indicate p<0.05, 0.01, and 0.001, respectively (unpaired t-test).

In addition, when 100 µM HC-030031 as an hTRPA1 antagonist was added, the $Ca^{2+}$ response by coniferyl alcohol was significantly reduced (FIG. 30).

15. Sensory Test

As a result of the sensory test of coniferyl alcohol, the intensity of pungent tastes (spicy, tingle, and tangy tastes) was shown to be 11.83±1.6. It was evaluated that the remaining taste was stronger than the first taste and the tongue burns or has a pain, as well as has acrid taste, bitter taste, spicy taste, and astringent taste. In addition, it was shown that there was a very strong tendency for the taste to remain in the mouth.

16. Lacrimation Test

As a result of testing ocular tears or irritation due to the spray of coniferyl alcohol, ocular pain (tingling, stinging, and dizziness) was observed. Like the sensory test, the intensity of the ocular pain was determined to be stronger later than at first, and the sensation had a strong tendency to remain for a long time.

17. Analysis of Effect on GLP-1 Secretion (Anti-Diabetic and Anti-Obesity Efficacies)

Figure 31:
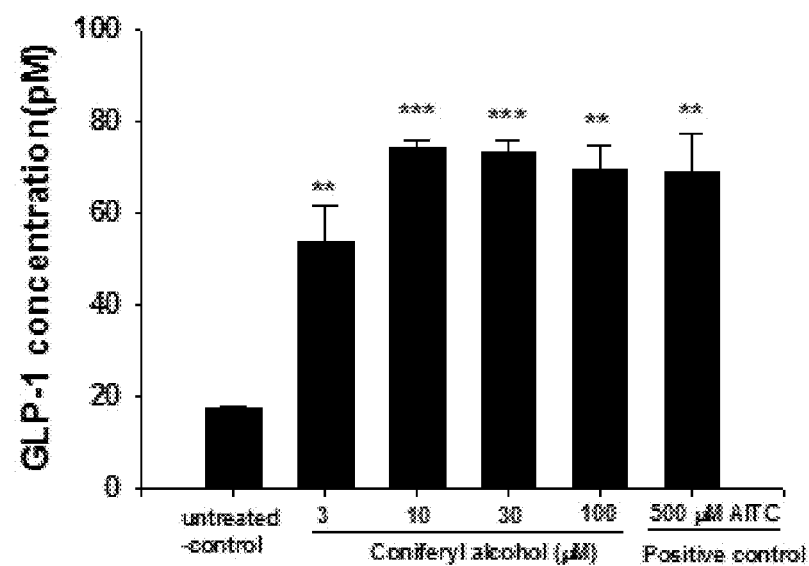
FIG. 31 is a graph showing results of GLP-1 secretion of NCI-H716 on coniferyl alcohol. Data were expressed by the mean±S.D. (n=3).  P<0.01; * P<0.001 vs. untreated control group.

The GLP-1 secretion for coniferyl alcohol was investigated using the NCI-H716 cell line. As a result, the GLP-1 secretion was shown to be 3 times higher in 3 µM coniferyl alcohol-treated group, and 4 times or higher in 10 µM or higher in coniferyl alcohol-treated group, as compared with the untreated control group (FIG. 31). The GLP-1 secretion was shown to be 3.9 times in 500 µM AITC used as a positive control group. Therefore, the coniferyl alcohol that promotes GLP-1 secretion can be expected to have anti-diabetic ad anti-obesity effect.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for treating a human suffering from obesity comprising administering a therapeutically effective amount of a Kalopanax pictus sprout extract to said human suffering from obesity to effectively treat the obesity in said human.

2. The method of claim 1, wherein said Kalopanax pictus sprout extract comprises coniferyl alcohol.

\* \* \* \* \*